(12) United States Patent
Chen et al.

(10) Patent No.: US 10,378,067 B2
(45) Date of Patent: Aug. 13, 2019

(54) KIT FOR CANCER DETECTION

(71) Applicant: Lihpao Life Science Corp., New Taipei (TW)

(72) Inventors: Chih-Hao Chen, New Taipei (TW); Meng-Ju Lee, New Taipei (TW); Chia-Lin Wu, New Taipei (TW); Yu-Wei Liu, New Taipei (TW)

(73) Assignee: LIHPAO LIFE SCIENCE CORP., New Taipei (TW)

( * ) Notice: Subject to any disclaimer, the term of this patent is extended or adjusted under 35 U.S.C. 154(b) by 221 days.

(21) Appl. No.: 15/511,292

(22) PCT Filed: Sep. 16, 2015

(86) PCT No.: PCT/CN2015/089729
§ 371 (c)(1),
(2) Date: Mar. 15, 2017

(87) PCT Pub. No.: WO2016/041495
PCT Pub. Date: Mar. 24, 2016

(65) Prior Publication Data
US 2017/0292164 A1    Oct. 12, 2017

Related U.S. Application Data

(60) Provisional application No. 62/050,963, filed on Sep. 16, 2014.

(51) Int. Cl.
*C12Q 1/68* (2018.01)
*C12Q 1/6886* (2018.01)

(52) U.S. Cl.
CPC ..... *C12Q 1/6886* (2013.01); *C12Q 2600/156* (2013.01); *C12Q 2600/158* (2013.01)

(58) Field of Classification Search
None
See application file for complete search history.

(56) References Cited

FOREIGN PATENT DOCUMENTS

| CN | 101608224 A | 12/2009 |
|----|-------------|---------|
| CN | 101974642 A | 2/2011 |
| CN | 102168128 A | 8/2011 |
| CN | 103374620 A | 10/2013 |
| CN | 103555826 A | 2/2014 |
| CN | 103865981 A | 6/2014 |
| EP | 2 784 164 A1 | 10/2014 |
| WO | WO 2004/050910 A1 | 6/2004 |
| WO | WO 2014/130890 A1 | 8/2014 |

OTHER PUBLICATIONS

Ohsawa et al; Molecular Medicine Reports, vol. 2, pp. 887-891, 2009.*
Newton et al; Nucleic Acids Research, vol. 17, pp. 2503-2516, 1989.*

* cited by examiner

*Primary Examiner* — Jehanne S Sitton
(74) *Attorney, Agent, or Firm* — Birch, Stewart, Kolasch & Birch, LLP.

(57) ABSTRACT

The present invention provides a primer set and a kit containing same for analyzing a sequence of an MLH1 DNA, an MLH1 mRNA, and/or a cDNA sequence derived from said MLH1 mRNA of a subject to identify a V384 alteration of an MLH1 gene encoded protein.

4 Claims, 8 Drawing Sheets
Specification includes a Sequence Listing.

KIT FOR CANCER DETECTION

CROSS REFERENCE TO RELATED APPLICATIONS

This application is the National Phase of PCT International Application No. PCT/CN2015/089729, filed on Sep. 16, 2015, which claims priority under 35 U.S.C. 119(e) to U.S. Provisional Application No. 62/050,963, filed on Sep. 16, 2014, all of which are hereby expressly incorporated by reference into the present application.

TECHNICAL FIELD

The present invention relates to a kit for cancer detection; more specifically, a detection kit having a primer set or probe targeting a V384D mutation.

DESCRIPTION OF RELATED ART

Cancer has been the leading cause of death for a long time in human history. Numberless researches are conducted focusing on the detection and treatment of cancers. Unfortunately, most of the treatments of cancer used clinically in nowadays still are not reliable for eliminating the threat of cancer. Nevertheless, researches and clinical experience have showed that the earlier the treatment begins, the higher the survival rate is for cancer patients. These evidences give the importance of the cancer detection especially at the early stage of carcinogenesis.

Typically, the detection of carcinogenesis is made by determining biomarkers specifically existing in cancer patients. The biomarkers might be the substances specifically released by cancer cells, the cell surface markers specifically expressed by cancer cells, the gene silence or overexpression specifically happened in cancer cells, or the gene mutation specifically existing in cancer cells.

The missense mutation in the DNA mismatch repair gene hMLH1 has been reported recently as a biomarker in several kinds of cancers. The missense mutation of V384D in hMLH1 was first observed in colorectal cancer and the occurrence thereof was showed to be specific in Chinese patients in comparison with German patients (Yaping Wang, et al, 1997). Subsequent studies had confirmed the aforesaid discovery and a further study in 2004 by Chang et al. even highlighted the missense mutation of hMLH1 V384D in four kinds of cancers including colorectal cancer, gastric cancer, breast cancer, and esophageal cancer and another study in 2003 by Xianzhe Shi et al also showed the existence in lung cancer.

The aforesaid studies indicated that the missense mutation of V384D in hMLH1 could be a promising candidate for cancer detection. Moreover, the research did by the team of the instant invention further proves that the missense mutation of V384D in hMLH1 is related to the drug resistance in the EGFR-TKIs treatment of lung cancer (data showed in the following paragraphs).

In light of the foregoing, the well-designed detection tools targeting the aforesaid V384D mutation shall be helpful and valuable medical industry and clinical use. Although several researches have presented some primers and probes for the aforesaid purpose, the goal of the present invention is to provide a primer set and/or a probe being more specific and sensitive than the conventional ones.

SUMMARY

In light of the foregoing, one of the objects of the present invention is to provide a kit for cancer detection by using a promising biomarker.

Another object of the present invention is to provide a kit for evaluating the efficacy of an EGFR-TKI treatment and/or the progression-free survival of a subject after the same so that the follow-up treating strategies can be set up as soon as possible after an EGFR-TKI treatment.

In order to achieve the above-mentioned objects, the present invention provides a kit for identifying a V384 alteration of a MLH1 gene encoded protein of a subject, comprising:

a first primer comprising a sequence of SEQ ID NO 06; and a second primer comprising a sequence of SEQ ID NO 07; and/or a first primer comprising a sequence of SEQ ID NO 08; and a second primer comprising a sequence of SEQ ID NO 09.

Preferably, said kit further comprises a third primer comprising a sequence of SEQ ID NO 05.

Preferably, said kit of claim 1, further comprising a DNA polymerase.

Preferably, said kit further comprises a double strands DNA binding dye.

Preferably, said double strands DNA binding dye is SYBR® Green I, SYBR® Green II, SYBR® Gold, Oxazole Yellow, Thiazole Orange, PicoGreen, EvaGreen®, a combination thereof.

The present invention also provides a kit for identifying a V384 alteration of a MLH1 gene encoded protein of a subject, comprising:

a first primer comprising a sequence of SEQ ID NO 08; and a second primer comprising a sequence of SEQ ID NO 09.

The present invention also provides kit for identifying a V384 alteration of a MLH1 gene encoded protein of a subject, comprising:

at least one mutation probe comprising a sequence of CAGATGGATC (SEQ ID NO 10); wherein said probe is conjugated with a fluorophore; and/or at least one wild-type probe comprising a sequence of CAGATGGTTC (SEQ ID NO 11); wherein said probe is conjugated with a fluorophore.

Preferably, said at least one mutation probe and/or said at least one wild-type probe is further conjugated with a quencher. Preferably, said fluorophore is conjugated at the 5' end of said probe and said quencher is conjugated at the 3' end of said probe. Preferably, said at least one mutation probe comprises a sequence of SEQ ID NO 17. Preferably, said at least one wild-type probe comprises a sequence of SEQ ID NO 16.

Preferably, said at least one mutation probe and/or at said at least one wild-type probe comprises at least one nucleotide thereof being modified with a bridge connecting the 2' oxygen and 4' carbon thereof. Preferably, said mutation probe comprises a sequence of SEQ ID NO 19 having the following sequence:

5'-CACCAGATGGATCGTACA-3'.

Preferably, said mutation probe has the 5th, 8th, 11th, and 14th nucleotides thereof counted from 5' to 3' being modified with a bridge connecting the 2' oxygen and 4' carbon.

Preferably, said wild-type probe comprises a sequence of SEQ ID NO 18 having the following sequence:

5'-CACCAGATGGTTCGTACA-3'.

Preferably, said mutation probe has the 5th, 8th, 11th, and 14th nucleotides thereof counted from 5' to 3' being modified with a bridge connecting the 2' oxygen and 4' carbon.

Preferably, said kit further comprises an anchor probe conjugated with a donor fluorophore. Preferably, said at least one mutation probe comprises a sequence of SEQ ID NO 21 and is conjugated with a receptor fluorophore. Preferably, said at least one wild-type probe comprises a sequence of SEQ ID NO 20 and is conjugated with a receptor fluorophore. Preferably, said anchor probe comprises a sequence of SEQ ID NO 22.

Preferably, said kit further comprises a primer set for amplifying at least a part of said MLH1 gene to obtain an amplicon; wherein said amplicon comprises a site corresponding to said V384 alteration.

Preferably, said primer set is:
a forward primer comprising a sequence of SEQ ID NO 12, and a reverse primer comprising a sequence of SEQ ID NO 13; and/or
a forward primer comprising a sequence of SEQ ID NO 14, and a reverse primer comprising a sequence of SEQ ID NO 15.

Preferably, said kit further comprises a DNA polymerase.

To sum up, the present invention provides a novel primer set or a probe for identifying a V384 alteration of a MLH1 gene and a kit having the same. By using the primer set and/or the kit of the present invention, the identification of the V384 alteration can be performed more specifically and sensitively than the conventional tools.

DETAILED DESCRIPTION

Figure 1:
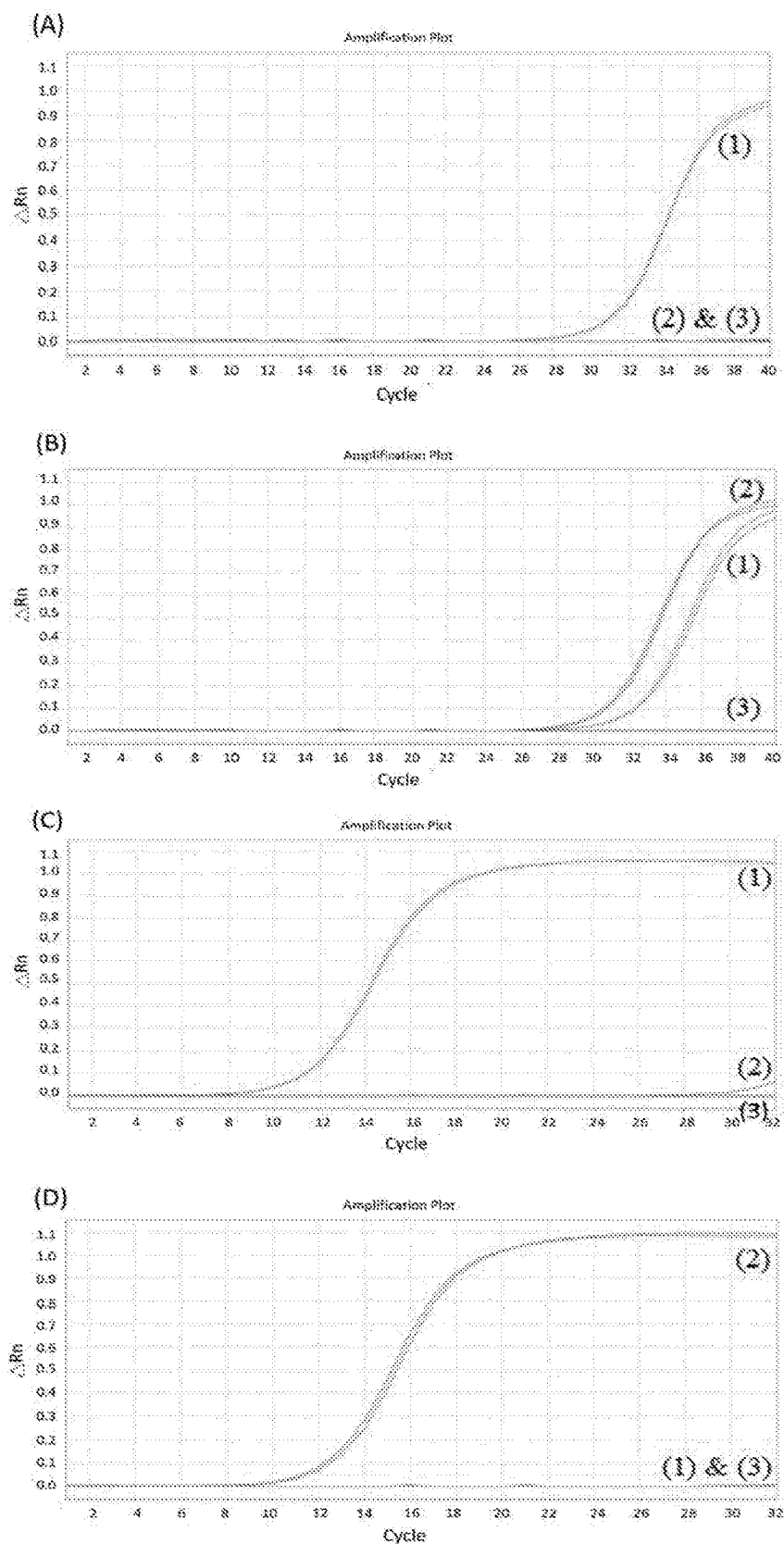
FIG. 1 shows the results of the Real-time polymerase chain reaction of the Example 1 of the instant specification (n=2); wherein the results of primer set of SEQ ID NO 07 and SEQ ID NO 06 were marked as curve (1), the results of primer set of SEQ ID NO 05 and SEQ ID NO 06 were marked as curve (2), and the results of negative control were marked as curve (3). (A) Genomic DNA of a subject without V384D mutation. (B) Genomic DNA of a subject with V384D mutation (heterozygote). (C) Artificial plasmid constructed with a partial sequence of a wild-type MLH1 gene (homozygote). (D) Artificial plasmid constructed with a partial sequence of a MLH1 gene with the T1151A mutation (homozygote).

In this study, we provided a primer set and/or a probe suitable for analyzing a sequence of a MLH1 DNA, a MLH1 mRNA, and/or a cDNA sequence derived from said MLH1 mRNA of a subject to identify a V384 alteration of a MLH1 gene encoded protein.

The identification of said alteration could provide a promised possibility that the subject to be detected has already had cancer, such as colorectal cancer, gastric cancer, breast cancer, esophageal cancer, lung cancer, or a combination thereof. Moreover, in terms of a lung cancer therapy, the identification of said alteration in a subject could also provide information for evaluating efficacy of an EGFR-TKI treatment and/or for evaluating progression-free survival of said subject after an EGFR-TKI treatment.

The term of "EGFR-TKI therapy" or "EGFR-TKI treatment" used herein is referred to as a targeted therapy or targeted treatment adopting the fact that a fair amount of non-small cell lung cancer patients share a somatic mutation in the tyrosine kinase domain of epidermal growth factor receptor of tumor cells. Specifically, the "EGFR-TKI therapy" or "EGFR-TKI treatment" is conducted by using an EGFR tyrosine kinase inhibitor targeting the somatic mutation in the tyrosine kinase domain of epidermal growth factor receptor of tumor cells.

The term of "efficacy of an EGFR-TKI treatment" used herein is referred to as the effect of an EGFR-TKI treatment on the progress of tumors. If tumors keep progressing within 3 months from the initiation of an EGFR-TKI treatment, the treatment is considered as clinically ineffective. On the other hand, if the tumors are at least 30% reduced in size (based on the initial size there of before treatment), the EGFR-TKI treatment is determined as having efficacy to the subject.

The term of "progression-free survival" used herein is referred to as the time period between the initial date of a treatment and the time point that the tumor concerned begins to progress again. In other words, it is the length of time that the tumors, during this time period, have no progress or are reduced in size.

The term of "analyzing" or "analyze" used herein is referred to as evaluating or examining a property of a subject of interest by at least of technical means. Said technical means include but not limited to polymerase chain reaction, Southern blot, and Western blot.

The description of "V384 alteration of a MLH1 gene encoded protein" recited herein is referred to as an alternation existing in the sequence of said MLH1 gene that results in an alteration at V384 position of a MLH1 gene encoded protein. In an alternative embodiment of the present invention, said V384 alteration is a V384D mutation of a protein encoded by said MLH1 gene. In an alternative embodiment, said V384D mutation can be identified as a T1151A mutation of a cDNA of said MLH1 gene, or a T1349A mutation of a RNA of said MLH1 gene. The term of "wild-type" is a comparative term for describing a gene and/or a protein without the aforesaid mutation/alternation.

The term of "V384" used herein is referred to as the 384$^{th}$ amino acid of the amino acid sequences of a MLH1 protein (that is, a protein encoded by said MLH1 gene); wherein "V" is the one-letter abbreviation of Valine (Val). The term of "V384 alteration" used herein is referred to as the 384$^{th}$ amino acid of Valine is altered to another amino acid other than Valine. The term of "V384D mutation" used herein is referred to as the 384$^{th}$ amino acid of Valine is altered to Aspartic acid; wherein "D" is the one-letter abbreviation of Aspartic acid (Asp). See also SEQ ID NO 01 for the amino acid sequence having the aforesaid mutation and SEQ ID NO 02 for the DNA sequence having the aforesaid mutation.

The term of "T1349" used herein is referred to as the 1349$^{th}$ nucleotide of the nucleotide sequence of a mRNA encoding a MLH1 protein; "T" is an abbreviation of thymine. The term of "T1349 mutation" used herein is referred to as the 1349$^{th}$ nucleotide of thymine is altered/mutated to another nucleotide other than thymine. The term of "T1349A mutation" used herein is referred to as the 1349$^{th}$ nucleotide of thymine is altered to adenine; wherein "A" is an abbreviation of adenine. See also SEQ ID NO 03 for the mRNA sequence having the aforesaid mutation.

The term of "T1151" used herein is referred to as the 1151$^{th}$ nucleotide of the nucleotide sequence of a cDNA; wherein said cDNA is from a mRNA of said MLH1 gene; "T" is an abbreviation of thymine. The term of "T1151 mutation" used herein is referred to as the 1151$^{th}$ nucleotide of thymine is altered/mutated to another nucleotide other than thymine. The term of "T1151A mutation" used herein is referred to as the 1151$^{th}$ nucleotide of thymine is altered to adenine; wherein "A" is an abbreviation of adenine. See also SEQ ID NO 04 for the cDNA sequence having the aforesaid mutation.

Primer Sets, Probes, and Kits Using the Same

First Aspect

In the first aspect of the present invention, the V384 alteration of a MLH1 gene encoded protein is detected by using a primer set. Said "V384 alteration of a MLH1 gene encoded protein" is defined as set forth in the preceded paragraphs. Preferably, the detection is conducted by real-time PCR with said primer set.

In the first aspect of the present invention, a kit for identifying a V384 alteration of a MLH1 gene encoded protein of a subject is provided. Said kit comprises a primer set, which is designed for analyzing a sequence of a MLH1 DNA, a MLH1 mRNA, and/or a cDNA sequence derived from said MLH1 mRNA of a subject to identify a V384 alteration of a MLH1 gene encoded protein.

In a preferable embodiment, said primer set comprises a first primer and a second primer. Said first primer is designed to comprise a sequence that is capable of hybridizing with a MLH1 gene having said V384 alteration at V384 site. Said second primer is designed to comprise a sequence that is capable of hybridizing with a conserved region of said MLH1 gene. The PCR product of said first primer and said second primer is detected representing the existence of the V384 alteration.

The term of "capable of hybridizing with a MLH1 gene having said V384 alteration at V384 site" means said sequence is capable of base-pairing with at least one nucleotide of the codon encoding said V384 alteration in said MLH1 gene. It is known that a codon contains three nucleotides. In a preferable embodiment, said sequence is capable of forming base-pairs with at least two nucleotides of the codon encoding said V384 alteration in said MLH1 gene.

The term of "a conserved region of said MLH1 gene" used herein is referred to a sequence of said MLH1 gene that is conserved or unchanged between a wild-type MLH1 gene and a MLH1 gene having the aforesaid V384 alteration. The term of "wild-type" is a relative description to describe a subject without the aforesaid V384 alteration.

In an alternative embodiment, said kit further comprises a third primer. Said third primer is designed to comprise a sequence that is capable of hybridizing with a wild-type MLH1 gene at the site of V384. The term "capable of hybridizing" is defined as preceded paragraphs.

In a practical embodiment, said kit comprises a first primer of SEQ ID NO 06, a second primer of SEQ ID NO 07, and a third primer of SEQ ID NO 05. This embodiment is used for a SYBR-green assay. The detection of the PCR product of said first primer and said second primer represents the existence of said V384 alteration while in this case the PCR product of said third primer and said second primer of SEQ ID NO 07 is a control.

In another practical embodiment, said kit comprises a first primer of SEQ ID NO 08 and a second primer of SEQ ID NO 09. This embodiment is used for a High Resolution Melting (HRM) assay. In a HRM assay, the DNA binding dye will bind to the PCR product at standard stage and the fluorescence can be detected. While in the melting stage, the PCT product is melted and a decay of the fluorescence signal of the DNA binding dye can be detected. By comparing the decay pattern of a sample with a wild-type control or a mutation control, the V384 alteration can be identified.

In a preferable embodiment, said kit further comprises a DNA polymerase, and/or a DNA binding dye. Preferably, said DNA polymerase is, but not limited to, Pfu DNA polymerase, Taq DNA polymerase or a combination thereof. Preferably, said DNA binding dye is, but not limited to, SYBR® Green I, SYBR® Green II, SYBR® Gold, Oxazole Yellow, Thiazole Orange, PicoGreen, EvaGreen®, or a combination thereof.

Second Aspect

In the second aspect of the present invention, the V384 alteration of a MLH1 gene encoded protein is detected by using a probe. Said "V384 alteration of a MLH1 gene encoded protein" is defined as set forth in the preceded paragraphs.

In the second aspect of the present invention, a kit for identifying a V384 alteration of a MLH1 gene encoded protein of a subject is provided.

In a preferable embodiment, said kit comprises a probe, which is designed for analyzing a sequence of a MLH1 DNA, a MLH1 mRNA, and/or a cDNA sequence derived from said MLH1 mRNA of a subject to positively or negatively identify a V384 alteration of a MLH1 gene encoded protein.

In a positive scenario of identifying V384 alteration, said probe (mutation probe) is designed to hybridize with a segment of a genomic DNA, a mRNA and/or a cDNA of said MLH1 gene; wherein said segment has a sequence corresponding to said V384 alternation of a protein encoded by said MLH1 gene. For example, said segment may have the T1349A mutation of said mRNA or the T1151A mutation of said cDNA. Through examining the result of hybridization, the aforesaid V384 alteration can be identified. In this positive scenario, the detection of the signal of hybridization between said probe and the target represents the existence of the V384 alteration. In a preferable embodiment, said mutation probe comprises a sequence of CAGATGGATC (SEQ ID NO 10).

In a negative scenario of identifying V384 alteration, said probe (wild-type probe) is designed to hybridize with a segment of a wild-type genomic DNA, a mRNA and/or a cDNA of said MLH1 gene. In this negative scenario, the inexistence of the signal of hybridization between said probe and the target represents the inexistence of wild-type MLH1 gene, giving possibility of the existence of the V384 alteration. In a preferable embodiment, said wild-type probe comprises a sequence of CAGATGGTTC (SEQ ID NO 11).

Nevertheless, those having skill in the art can realize that there is a possibility that the subject be tested may have a heterozygous genotype of MLH1 gene. That is, an allele of the MLH1 gene the subject has is wild-type while the other allele thereof is of a V384 alteration. In that circumstance, it is preferable to use a mutation probe or use both of the mutation probe and wild-type probe for detection.

Preferably, said probe (mutation probe and wild-type probe) is modified to fulfill the purpose of targeting the V384 alternation of said MLH1 gene. In an embodiment of the present invention, said probe is conjugated with a fluorophore and/or isotope. In a preferable embodiment, said probe is conjugated with a fluorophore and a quencher. In an alternative embodiment, said probe is further modified with a bridge connecting the 2' oxygen and 4' carbon thereof.

Preferably, said fluorophore is conjugated at the 5' end of said probe and said quencher is conjugated at the 3' end of said probe. Said fluorophore includes, but not limited to 6-carboxyfluorescein, tetrachlorofluorescein, FAM, VIC, LC640, or a combination thereof. Said quencher includes, but not limited to tetramethylrhodamine, BHQ1, or a combination thereof.

In a preferable embodiment, said kit is designed for a PCR-based TaqMan assay. Said kit comprises a mutation probe comprising a sequence of SEQ ID NO 17, and/or a wild-type probe comprising a sequence of SEQ ID NO 16. Both of said probe are conjugated with a fluorophore and a quencher respectively at both ends of said probe.

In a preferable embodiment, said kit is designed for a PCR-based LNA assay (locked nucleic acid). Said kit comprises a mutation probe comprising a sequence of SEQ ID NO 19, and/or a wild-type probe comprising a sequence of SEQ ID NO 18. Both of said probe are conjugated with a fluorophore and a quencher respectively at both ends of said probe.

Preferably, said probe of SEQ ID NO 19 or SEQ ID NO 18 has at least one nucleotide being modified with a bridge connecting the 2' oxygen and 4' carbon thereof to form a locked nucleic acid. For instance, the $5^{th}$, $8^{th}$, $11^{th}$, and $14^{th}$ nucleotides of said probe (counted from 5' to 3') are modified with a bridge connecting the 2' oxygen and 4' carbon thereof.

In an alternative embodiment, said kit is designed for a PCR-based FRET assay (Fluorescence resonance energy transfer). In a practically embodiment, said kit comprises a mutation probe and/or a wild-type probe, and an anchor probe. Said mutation probe or wild-type probe is conjugated with a first fluorophore as a receptor and said anchor is conjugated with a second fluorophore as a donor. Preferably, said mutation probe comprises a sequence of SEQ ID NO 21, said wild-type probe comprises a sequence of SEQ ID NO 20, and said anchor probe comprises a sequence of SEQ ID NO 22. In a preferable embodiment, said kit comprises said mutation probe, said wild-type probe, and said anchor probe.

In a preferable embodiment, said first fluorophore is FAM, HEX, LC Red 640, Cy5, or a combination thereof. In a preferable embodiment, said second fluorophore is fluorescein or a combination thereof.

In an alternative embodiment, said kit further comprises a DNA polymerase. Preferably, said DNA polymerase has exonuclease activity.

In a preferably embodiment, said kit further comprises a primer set for amplifying a part of said MLH1 gene to obtain an amplicon; wherein said amplicon comprises a site corresponding to said V384. Said primer set may be:
    a first primer of SEQ ID NO 12 and a second primer of SEQ ID NO 13; and/or
    a first primer of SEQ ID NO 14 and a second primer of SEQ ID NO 15.

The following Table 1 lists the afore-mentioned primer sets and probes of the present invention together with the technology method therefor.

TABLE 1

Primer sets and Probes of the present invention listed correspondingly with the technology methods

| Methods | Primer name | Primer sequence | SEQ ID NO | Probe name | Probe sequence | SEQ ID NO |
|---|---|---|---|---|---|---|
| SYBR green 1 | SB-WT-sF3 | GGTCTATGCCCACC AGATTGT | 05 | N/A | N/A | |
| | SB-WT-sF3 | GGTCTATGCCCACC AGATTGA | 06 | | | |
| | SB-sR3 | GTTCAAGCATCTCC TCATCTG | 07 | | | |
| HRM | HR-1-F | TTCTGGAAGTAGTG ATAAGGTCTATGCC | 08 | N/A | N/A | |
| | HR-1-R | GGTTTGCTCAGAGG CTGCA | 09 | | | |
| TaqMan | TP-2-F | GGAAGTAGTGATAA GGTCTA | 12 | ML-TP-Wt | CCACCAGATGGTTCG TACAGATT | 16 |
| | TP-1-R | CTGTCTTATCCTCT GTGA | 13 | ML-TP-Mt | CCACCAGATGGATCG TACAGATT | 17 |
| LNA | TP-2-F | GGAAGTAGTGATAA GGTCTA | 12 | ML-LNA-Wt | CACCAGATGGTTCGT ACA | 18 |

TABLE 1-continued

Primer sets and Probes of the present invention
listed correspondingly with the technology methods

| Methods | Primer name | Primer sequence | SEQ ID NO | Probe name | Probe sequence | SEQ ID NO |
|---|---|---|---|---|---|---|
| | TP-1-R | CTGTCTTATCCTCTGTGA | 13 | ML-LNA-Mt | CACCAGATGGATCGTACA | 19 |
| FRET | FR-1-F | TAAATCCACAACAAGTCT | 14 | ML-sensor-Wt | ACCAGATGGTTCGTACAGAT | 20 |
| | FR-1-R | TAGAAATATCTGTCTTATCCT | 15 | ML-sensor-Mt | ACCAGATGGATCGTACAGAT | 21 |
| | | | | ML-anchor | CTTCTGGAAGTAGTGATAAGGTCTATGCC | 22 |

Example 1: Verification of the Primer Set Designed in the Present Invention (SYBR Green Assay)

In this example, the primers of SB-MT-sF3 (SEQ ID NO 06), SB-sR3 (SEQ ID NO 07), and SB-WT-sF3 (SEQ ID NO 05) were used for a Real-time polymerase chain reaction in order to verify their capability in identifying the V384D mutation.

For the experiments, four templates were prepared including a genomic DNA extracted from a subject without V384D mutation, a genomic DNA extracted from a subject with V384D mutation (heterozygote), an artificial plasmid constructed with a partial sequence of a wild-type MLH1 gene (homozygote), and an artificial plasmid constructed with a partial sequence of a MLH1 gene with the T1151A mutation (homozygote). The templates and the primer set used in this example were listed in the following Table 2.

TABLE 2

| | Primer Set | | |
|---|---|---|---|
| Template | Curve (1), FIG. 1 | Curve (2), FIG. 1 | Curve (3), FIG. 1 |
| Genomic DNA Subject w/o mutation | SEQ ID NO 05 SEQ ID NO 07 | SEQ ID NO 06 SEQ ID NO 07 | None (Negative control) |
| Genomic DNA Subject w/ mutation | SEQ ID NO 05 SEQ ID NO 07 | SEQ ID NO 06 SEQ ID NO 07 | None (Negative control) |
| Plasmid wild-type MLH 1 | SEQ ID NO 05 SEQ ID NO 07 | SEQ ID NO 06 SEQ ID NO 07 | None (Negative control) |
| Plasmid mutated MLH 1 | SEQ ID NO 05 SEQ ID NO 07 | SEQ ID NO 06 SEQ ID NO 07 | None (Negative control) |

The experiments were conducted according to the product manual of the EZtime™ Real Time PCR premix (Yeastern Biotech Co., Ltd.). The PCR mixture contained: 1.0 μl of template (2.5 μg/μl for genomic DNA template; 1 μg/μl for plasmid template), 12.5 μl of 2× EZtime Real-time PCR Premix, 1.0 μl of forward primer (5 μM), 1.0 μl of reverse primer (5 μM), and 9.5 μl of ddH$_2$O was prepared. The reaction condition was: 95° C. denaturation for 10 min; 95° C. denaturation 20 sec, 66° C. anneal/extension 1 min, 40 cycles; then melt curve stage: 95° C. 15 sec, 60° C. 1 min, 95° C. 30 sec, 60° C. 15 sec. The Real-time PCR instrument used was 7500 Fast (Applied Biosystem) equipped with Open 7500 Software v2.0.6.

The results were showed in FIG. 1 (A) to (D); wherein the results of primer set of SEQ ID NO 07 and SEQ ID NO 06 were marked as curve (1), the results of primer set of SEQ ID NO 05 and SEQ ID NO 06 were marked as curve (2), and the results of negative control were marked as curve (3).

According to the results, the wild-type primer set (SEQ ID NO 05 and SEQ ID NO 07) could only amplify the wild-type MLH1 sequence (FIGS. 1A, 1B, and 1C) and the mutant primer set (SEQ ID NO 06 and SEQ ID NO 07) could only amplify the MLH1 sequence with V384D mutation (FIGS. 1B and 1D). The amplification plot of FIG. 1A only showed curve (1) representing that it was indeed a homozygous wild-type sample. On the other hand, the amplification plot of FIG. 1B showed both curve (1) and curve (2) representing that it was a heterozygous sample. FIGS. 1C and 1D of artificial plasmids respectively showed curve (1) and curve (2) indicating that both of them were homozygotes.

The data showed that the present mutant primer set can specifically identify the V384D mutation of a MLH1 gene and the present wild-type primer set can specifically identify a MLH1 gene without the V384D mutation. The results proved that the primer set of the present invention could clearly identify the V384D mutation of a sample with excellent specificity and sensitivity.

Example 2: Verification of the Primer Set Designed in the Present Invention (HRM Assay)

In this example, the primers of HR-1-F (SEQ ID NO 08) and HR-1-R (SEQ ID NO 09) were used for a Real-time polymerase chain reaction in order to verify their capability in identifying the V384D mutation.

For the experiments, two templates were respectively an artificial plasmid constructed with a partial sequence of a wild-type MLH1 gene (homozygote) and an artificial plasmid constructed with a partial sequence of a MLH1 gene with the T1151A mutation (homozygote).

The experiments were conducted according to the product manual. Briefly, the PCR mixture contained: template 20 ng, Brilliant HRM Ultra-Fast Loci Master Mix, forward primer (HR-1-F) 0.5 uM, and reverse primer (HR-1-R) 0.5 uM. Reaction conditions: 95° C. pre-incubation for 3 min; 95° C. denaturation 5 sec, 60° C. anneal/extension 10 sec, 40 cycles; then melt curve stage: 95° C. 30 sec, 65° C. 30 sec, 95° C. 30 sec. Real-time PCR instrument is Agilent Mx3000p (Applied Biosystem). Open Applied Biosystem Software, and set the conditions in accordance with the above parameters.

Figure 2:
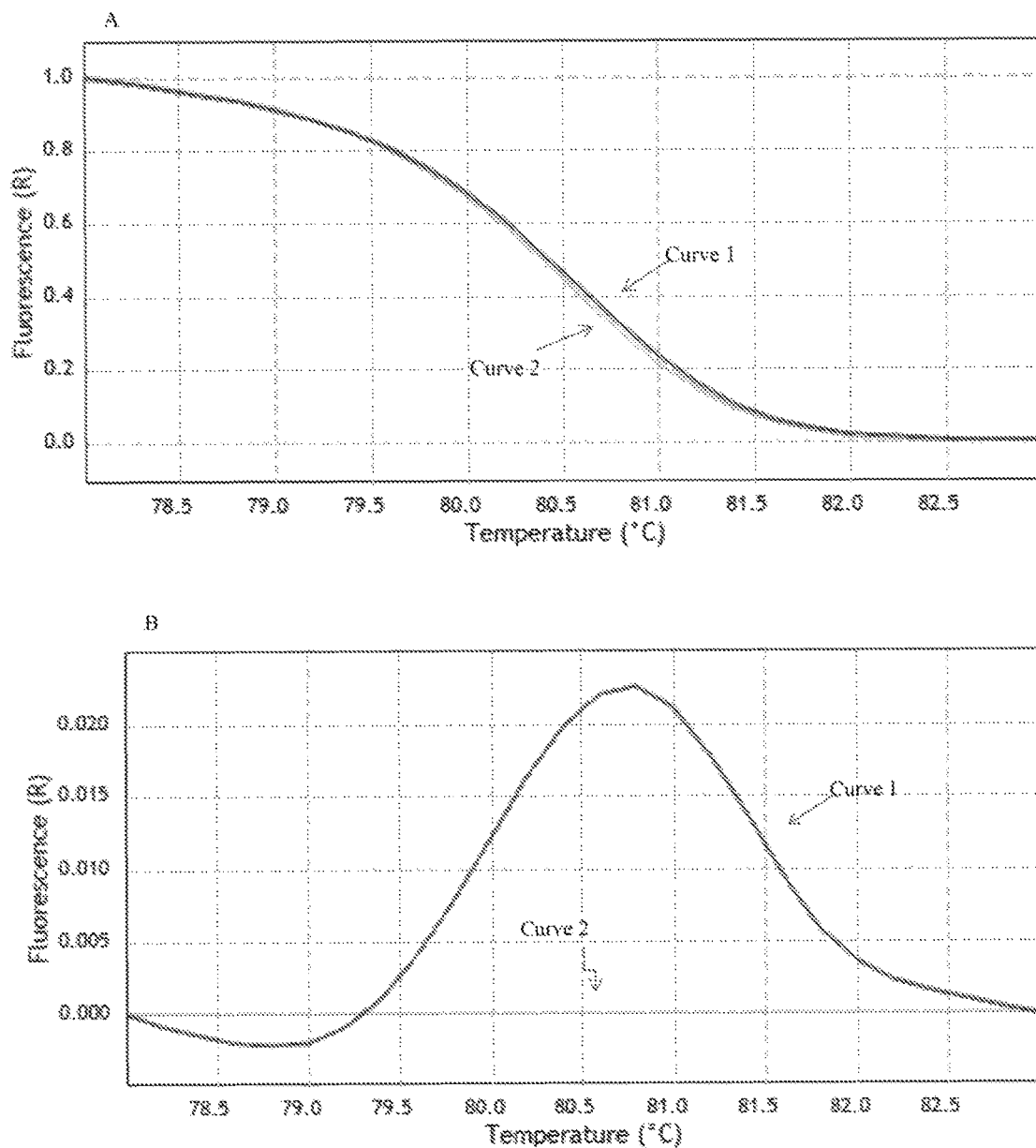
FIG. 2 showed the result of the HRM assay in Example 2 (n=2). (A) Standard stage; (B) Melt curve stage. Curve 1: Artificial plasmid constructed with a partial sequence of a wild-type MLH1 gene (homozygote). Curve 2: Artificial plasmid constructed with a partial sequence of a MLH1 gene with the T1151A mutation (homozygote).

FIG. 2 showed the result of the HRM assay of this example. It was noted that the primer set (HR-1-F and HR-1-R) was able to amplify both of the wild-type MLH1 sequence and the MLH1 sequence of V384D mutation (FIG. 2(A)). In the melting stage, mutant type had a mismatch nucleotide so it may have different dissociated curve from wild type. The decay of the signal shown as curve 2 represented the mutant existing (FIG. 2(B)). The result verified that the present primer set indeed recognized the V384 mutation.

Example 3: Verification of the Probe Designed in the Present Invention (TaqMan Assay)

In this example, the primers of TP-2-F (SEQ ID NO 12) and TP-1-R (SEQ ID NO 13) were used for a Real-time polymerase chain reaction. Also, a mutation probe (ML-TP-Mt; labeled with VIC and TAMRA) of SEQ ID NO 17 and a wild-type probe (ML-TP-Wt; labeled with FAM and TAMRA) of SEQ ID NO 16 were used to verify their capability in identifying the V384D mutation.

For the experiments, two templates were respectively an artificial plasmid constructed with a partial sequence of a wild-type MLH1 gene (homozygote) and an artificial plasmid constructed with a partial sequence of a MLH1 gene with the T1151A mutation (homozygote).

The experiments were conducted according to the product manual. Briefly, the PCR mixture contained: template 2.0 ul (25 ng/ul), 2× Brilliant III Ultra-Fast QPCR Master Mix with Low ROX 10.0 ul, 1.0 ul forward primer (10 uM), 1.0 ul reverse primer (10 uM), 0.5 ul ML-TP-Wt (10 uM), 0.5 ul ML-TP-Mt (10 uM), ddH$_2$O 5.0 ul. Reaction conditions: 95° C. denaturation for 3 min; 95° C. denaturation 12 sec, 55° C. anneal 30 sec, 72° C. extension 1 min, 40 cycles. Real-time PCR instrument is 7500 Fast (Applied Biosystem). Open 7500 Software v2.0.6, and set the conditions in accordance with the above parameters.

Figure 3:
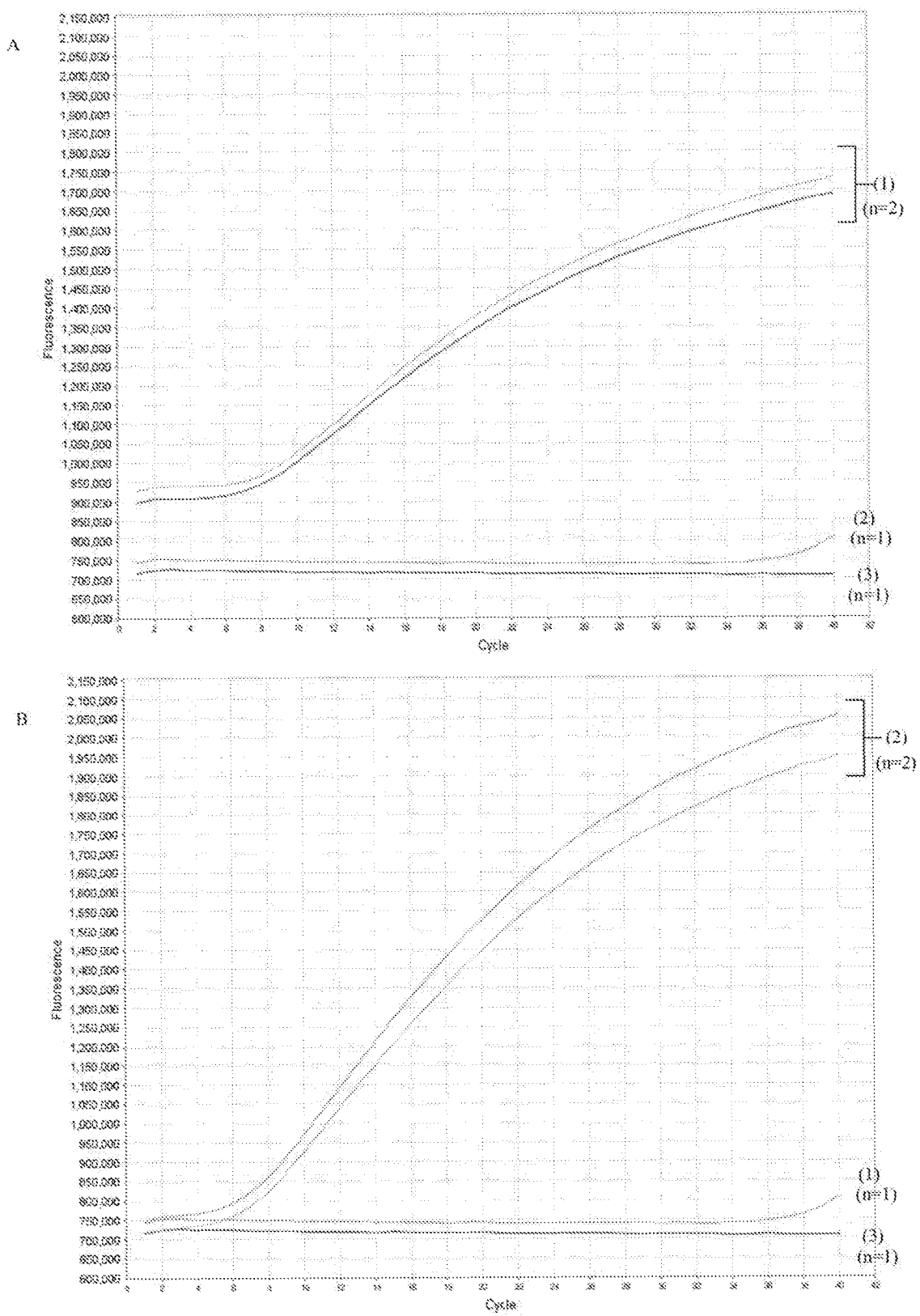
FIG. 3 showed the result of the TaqMan assay in Example 3 (n=2). (A): Artificial plasmid constructed with a partial sequence of a wild-type MLH1 gene (homozygote). (B) Artificial plasmid constructed with a partial sequence of a MLH1 gene with the T1151A mutation (homozygote). Curve (1): wild-type probe (negative probe, ML-TP-Wt, SEQ ID NO 16); curve (2): mutation probe (positive probe, ML-TP-Mt, SEQ ID NO 17); curve (3): control (no probes used).

The results were shown in FIG. 3. The wild-type MLH1 sequence could specifically detect by ML-TP-Wt probe (FIG. 3(A)), and the mutant MLH1 sequence could specifically detect by ML-TP-Mt probe (FIG. 3(B)). The result verified that the present probes have great specificity in detecting the V384 mutation.

Example 4: Verification of the Probe Designed in the Present Invention (LNA Assay)

In this example, the primers of TP-2-F (SEQ ID NO 12) and TP-1-R (SEQ ID NO 13) were used for a Real-time polymerase chain reaction. Also, a mutation probe (ML-LNA-Mt; labeled with VIC and BHQ1) of SEQ ID NO 19 and a wild-type probe (ML-LNS-Wt; labeled with FAM and BHQ1) of SEQ ID NO 18 were used to verify their capability in identifying the V384D mutation.

For the experiments, two templates were respectively an artificial plasmid constructed with a partial sequence of a wild-type MLH1 gene (homozygote), and an artificial plasmid constructed with a partial sequence of a MLH1 gene with the T1151A mutation (homozygote).

The experiments were conducted according to the product manual. Briefly, the PCR mixture contained: template 5.0 ul (2.5 ng/ul) or control plasmid DNA 5.0 ul (2.5 ng/ul), 2× EZtime Real-time PCR Premix 12.5 ul, 1.0 ul forward primer (10 uM), 1.0 ul reverse primer (10 uM), 0.5 ul ML-LNA-Wt (10 uM), 0.5 ul ML-LNA-Mt (10 uM), ddH$_2$O 4.5 ul. Reaction conditions: 95° C. denaturation for 10 min; 95° C. denaturation 15 sec, 50° C. anneal, 72° C. extension 1 min, 40 cycles; then melt curve stage: 95° C. 15 sec, 60° C. 1 min, 95° C. 30 sec, 60° C. 15 sec. Real-time PCR instrument is 7500 Fast (Applied Biosystem). Open 7500 Software v2.0.6, and set the conditions in accordance with the above parameters.

Figure 4:
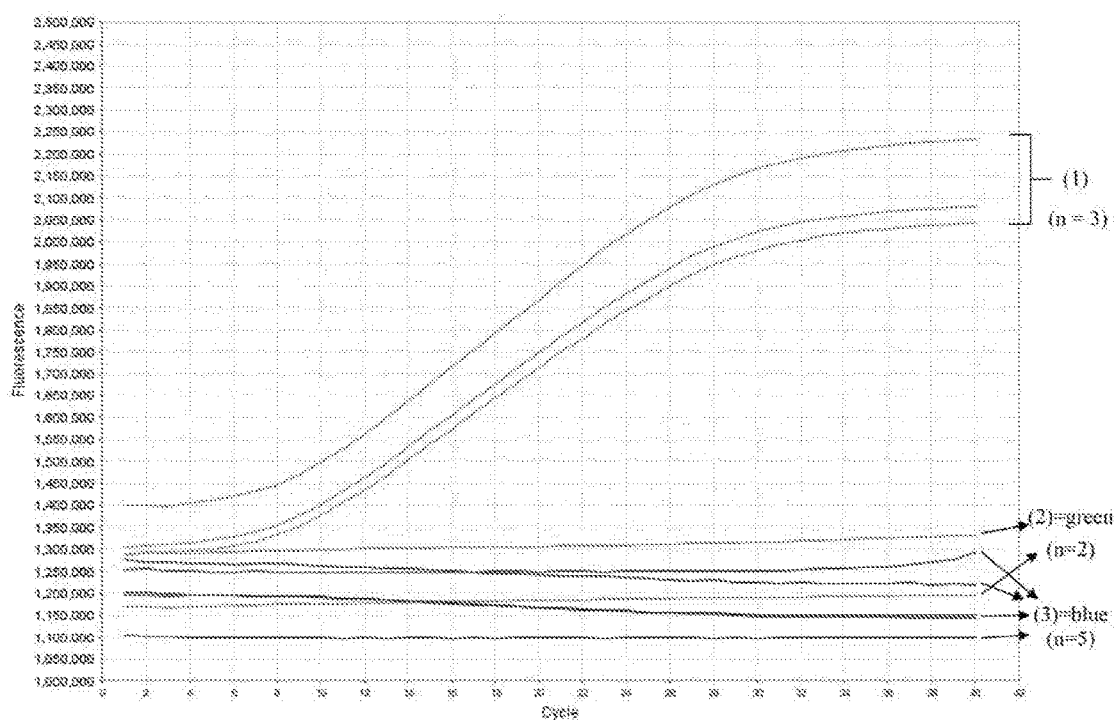
FIG. 4 showed the result of the LNA assay in Example 4 (n=3). (A): Artificial plasmid constructed with a partial sequence of a wild-type MLH1 gene (homozygote). (B) Artificial plasmid constructed with a partial sequence of a MLH1 gene with the T1151A mutation (homozygote). Curve (1): wild-type probe (negative probe, ML-TP-Wt, SEQ ID NO 18); curve (2): mutation probe (positive probe, ML-TP-Mt, SEQ ID NO 19); curve (3): control (no probes used).
Figure 4:
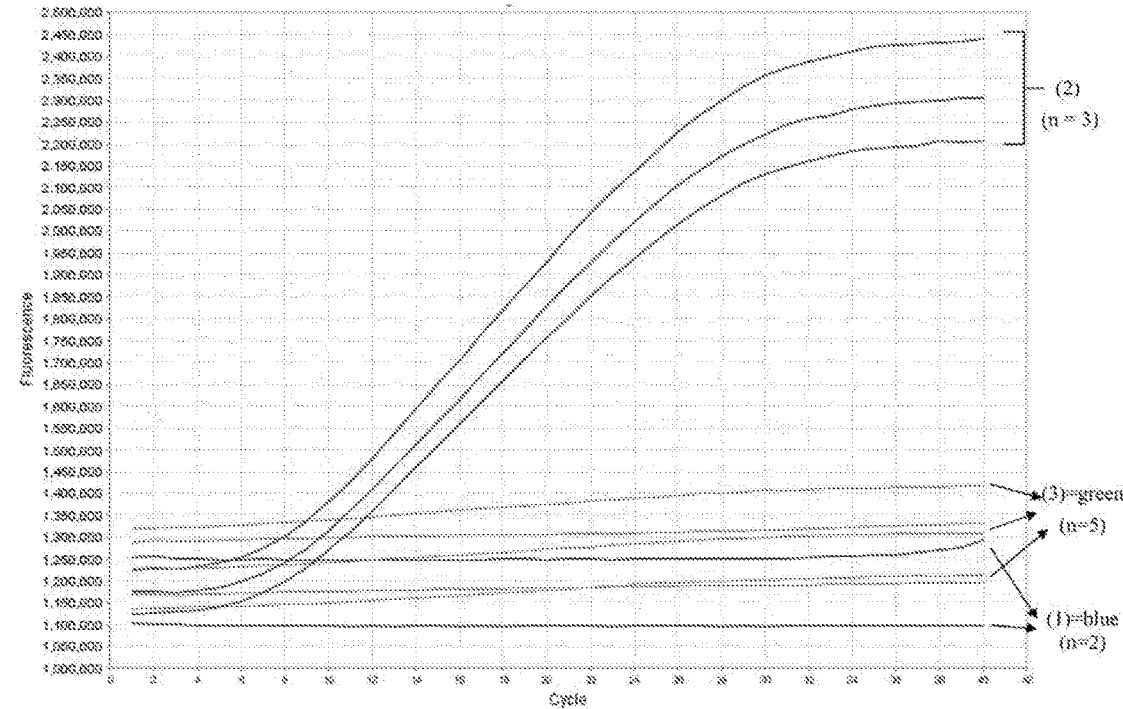

The results were shown in FIG. 4. The wild-type MLH1 sequence could specifically detect by ML-LNA-Wt probe (FIG. 4(A)), and the mutant MLH1 sequence could specifically detect by ML-LNA-Mt probe (FIG. 4(B)). The result verified that the present probes have great specificity in detecting the V384 mutation.

Example 5: Verification of the Probe Designed in the Present Invention (FRET Assay)

In this example, the primers of FR-1-F (SEQ ID NO 14) and FR-1-R (SEQ ID NO 15) were used for a Real-time polymerase chain reaction. Also, a mutation probe (ML-sensor-Mt; labeled with LC640) of SEQ ID NO 21, a wild-type probe (ML-sensor-Wt; labeled with LC640) of SEQ ID NO 20, and an anchor probe (ML-anchor; labeled with fluorescein) of SEQ ID NO 22 were used to verify their capability in identifying the V384D mutation.

For the experiments, two templates were respectively an artificial plasmid constructed with a partial sequence of a wild-type MLH1 gene (homozygote) and an artificial plasmid constructed with a partial sequence of a MLH1 gene with the T1151A mutation (homozygote). Furthermore, two clinical samples (VP13_0055 and VP13_0052) were also used. VP13_0055 is a homozygous wild-type and VP13_0052 is a heterozygous mutant confirmed by our previous data using next-generation sequencer (Ion PGM System; data not shown).

The experiments were conducted according to the product manual. Briefly, the PCR mixture contained: template 5.0 ul (2.5 ng/ul), 10× LightCycler FastStart DNA Master Hyb-Probe 2.0 ul, 1.0 ul forward primer (10 uM; SEQ ID NO 14), 1.0 ul reverse primer (10 uM; SEQ ID NO 15), 0.4 ul ML-sensor-Wt (10 uM), 0.4 ul ML-sensor-Mt (10 uM), 0.4 ul ML-anchor (10 uM), ddH$_2$O 8.6 ul. Reaction conditions: 95° C. denaturation for 10 min; 95° C. denaturation for 10 sec, 55° C. anneal for 10 sec, 72° C. extension for 30 sec, 45 cycles; then melt curve stage: 95° C. 1 min, 40° C. 2 min, 95° C. 1 min. Real-time PCR instrument is LightCycler 480 Real-Time PCR System (Roche). Open LightCycler 480 software 1.5, and set the conditions in accordance with the above parameters.

Figure 5:
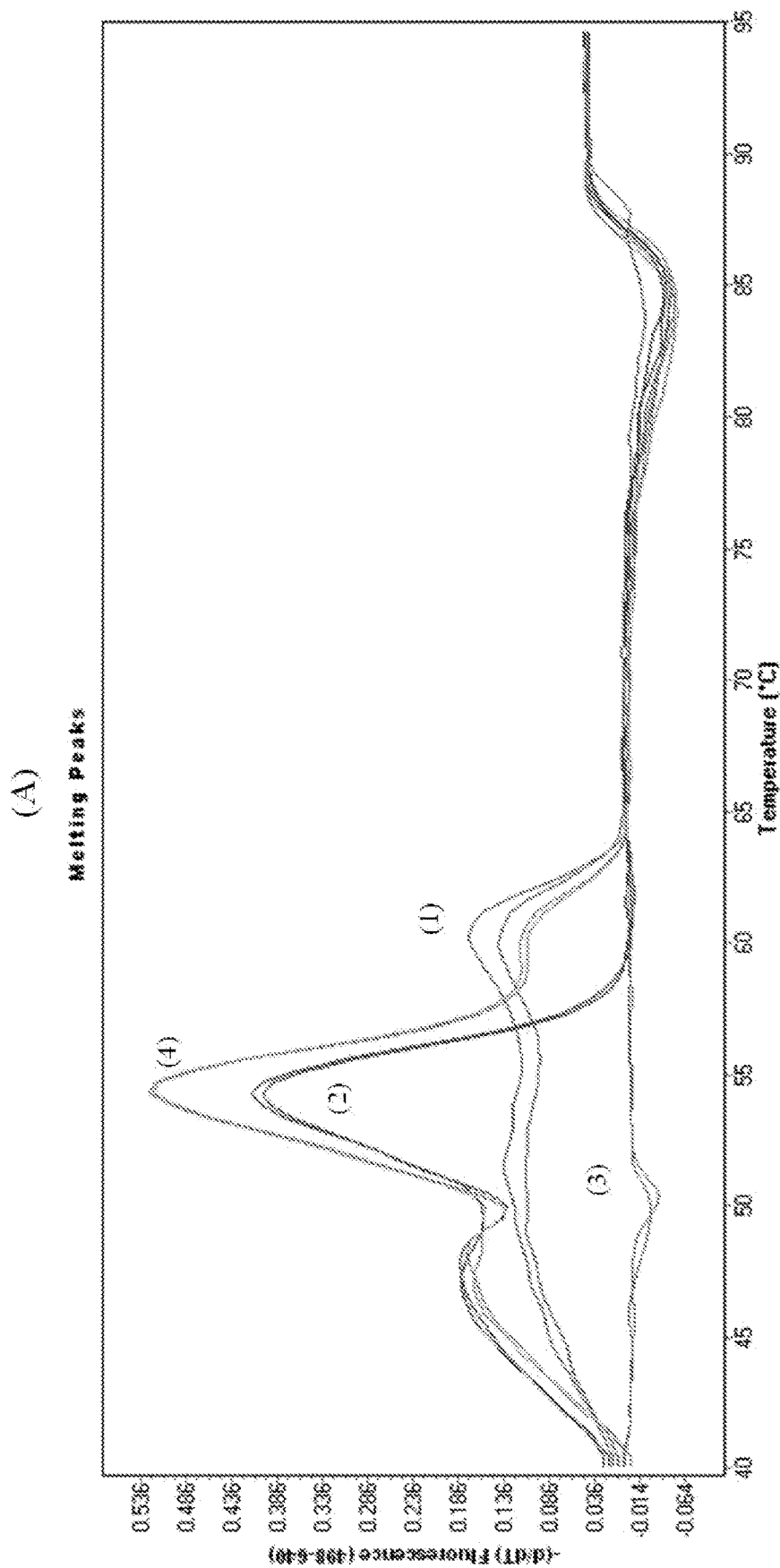
FIG. 5 showed the result of the FRET assay in Example 5 (n=2). (A)(B): probes of ML-sensor-Wt (SEQ ID NO 20) and ML-anchor (SEQ ID NO 22) were used; (C)(D): probes of ML-sensor-Mt (SEQ ID NO 21) and ML-anchor (SEQ ID NO 22) were used. Curve (1): Artificial plasmid constructed with a partial sequence of a wild-type MLH1 gene (homozygote). Curve (2): Artificial plasmid constructed with a partial sequence of a MLH1 gene with the T1151A mutation (homozygote). Curve (3): control (no template used). Curve (4): VP13_0052 (heterozygote). Curve (5): VP13_0055 (wild-type; homozygote).
Figure 5:
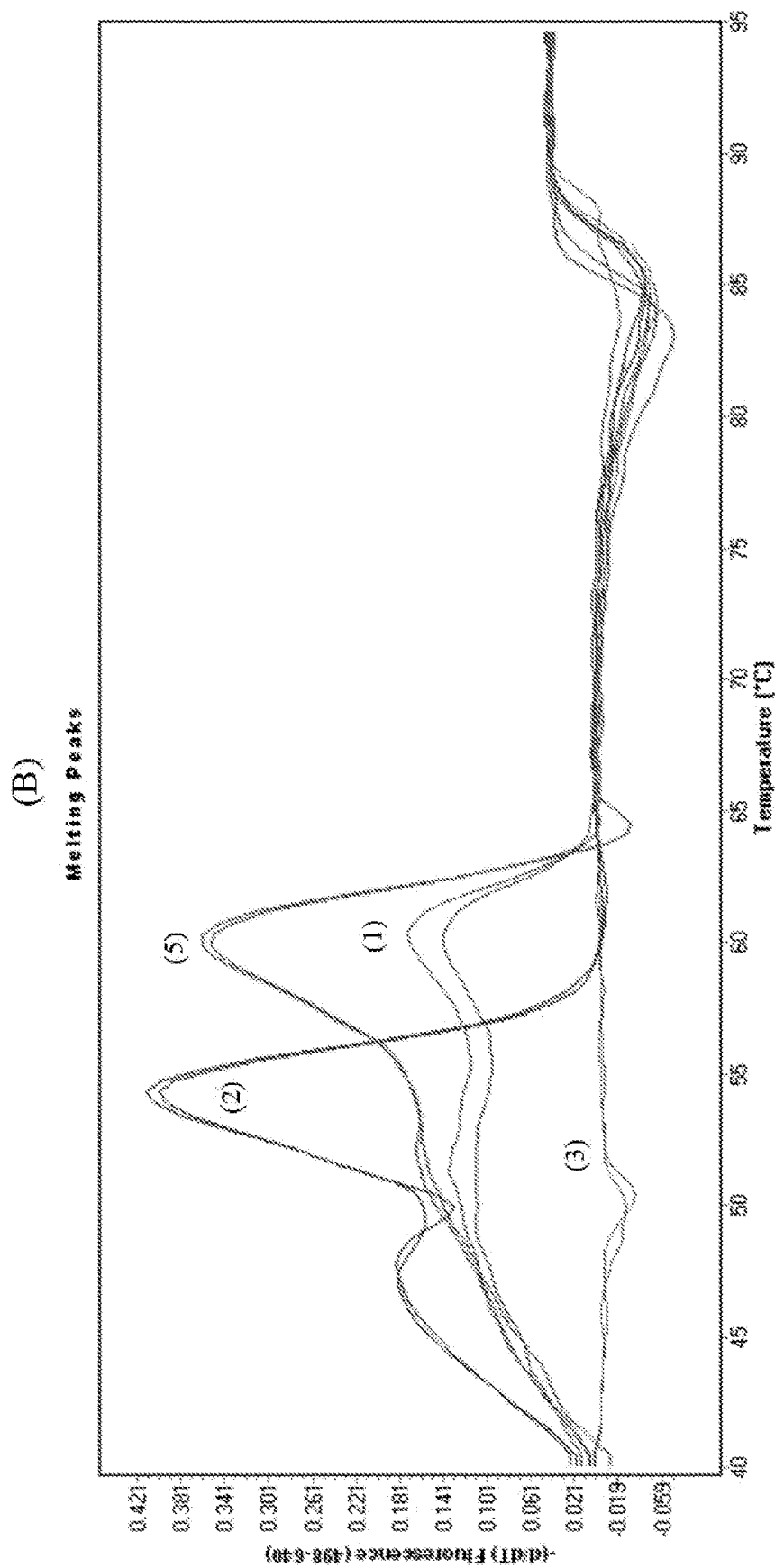
Figure 5:
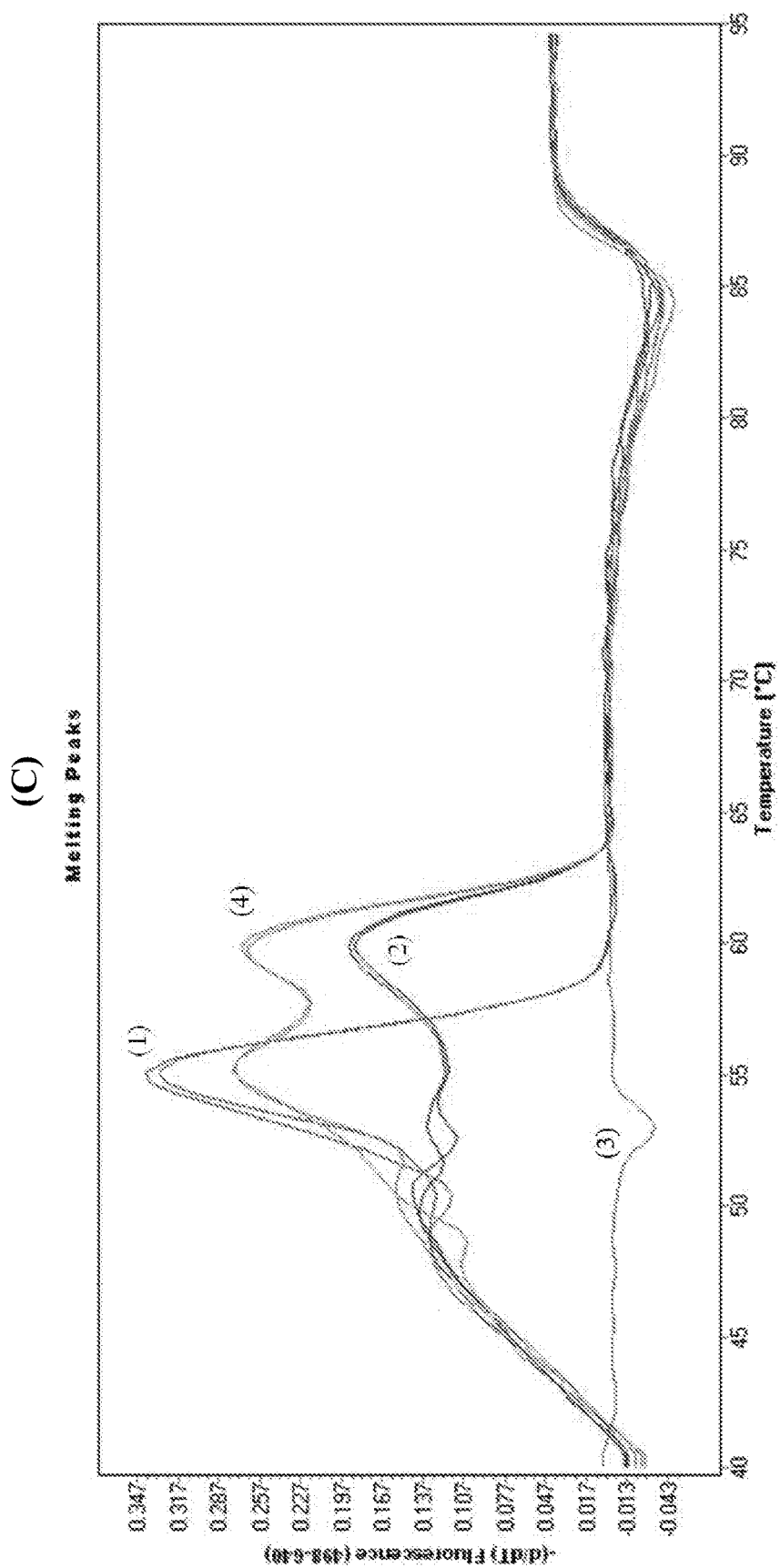
Figure 5:
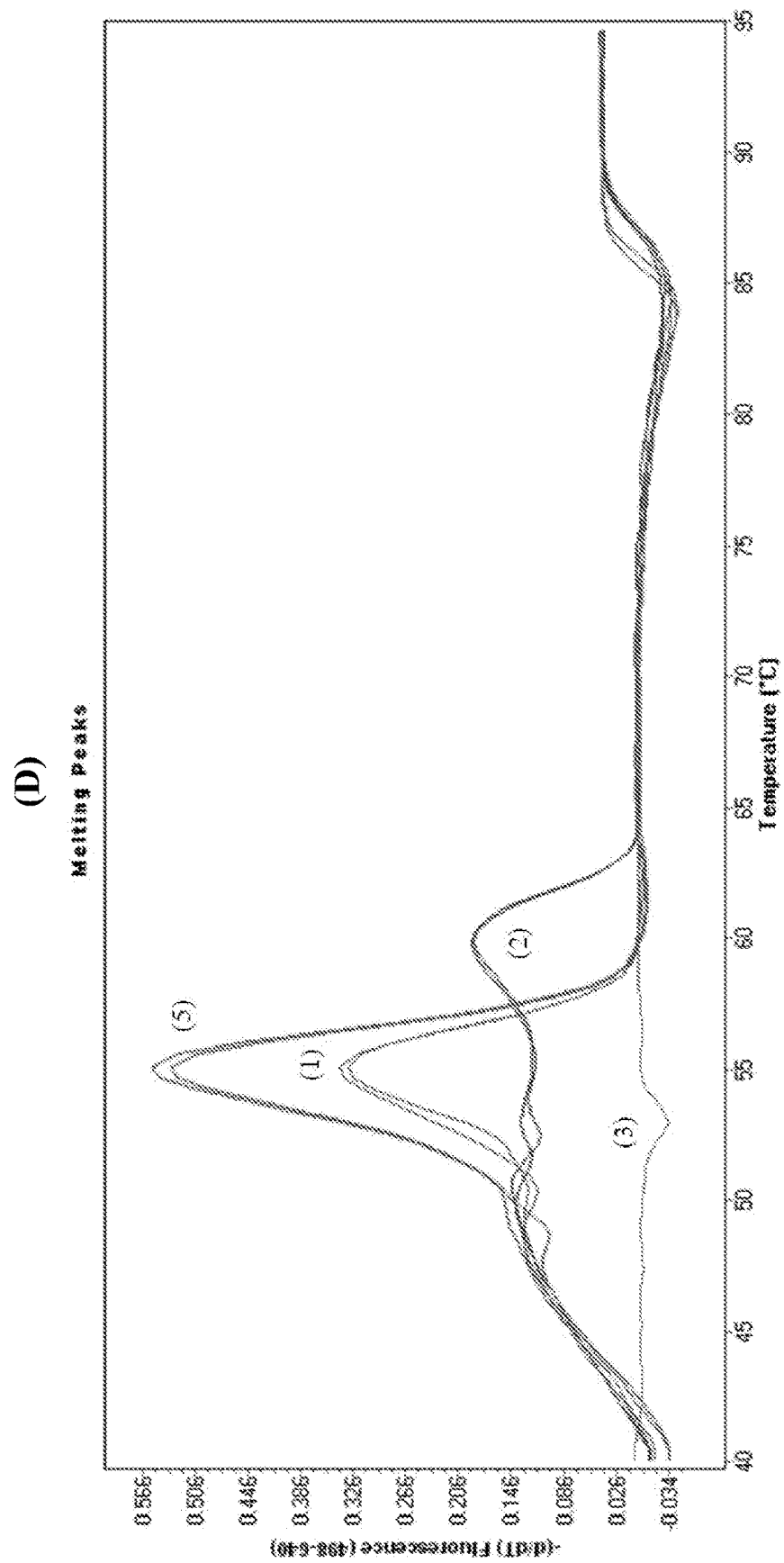

The results were shown in FIG. 5. The wild-type MLH1 sequence was detected by ML-sensor-Wt and ML-anchor, and the mutant MLH1 sequence was detected by ML-sensor-Mt and ML-anchor. When ML-sensor-Wt and ML-anchor were used, it was noted that both of the wild-type plasmid (curve 1) and VP13_0055 (curve 5) showed melting curve (FIGS. 5 (A) and (B)). When ML-sensor-Mt and ML-anchor were used, it was noted that both of the mutation plasmid (curve 2) showed melting curve (FIGS. 5 (C) and (D)). Moreover, VP13_0052 (curve 4), as being a heterozygote, showed melting curve no matter ML-sensor-Wt and ML-anchor or ML-sensor-Mt and ML-anchor were used (FIGS. 5 (A) and (C)). The result verified that the present probes have great specificity in detecting the V384 mutation.

The invention claimed is:

1. A kit for identifying a V384 alteration of a MLH1 gene encoded protein of a subject, comprising:
   a first primer comprising a sequence of SEQ ID NO 06; and
   a second primer comprising a sequence of SEQ ID NO 07.

2. The kit of claim 1, further comprising a third primer comprising a sequence of SEQ ID NO 05.

3. The kit of claim 1, further comprising a DNA polymerase.

4. The kit of claim 1, further comprising a double stranded DNA binding dye.

* * * * *

SEQUENCE LISTING

<160> NUMBER OF SEQ ID NOS: 22

<210> SEQ ID NO 1
<211> LENGTH: 756
<212> TYPE: PRT
<213> ORGANISM: Homo sapiens

<400> SEQUENCE: 1

```
Met Ser Phe Val Ala Gly Val Ile Arg Arg Leu Asp Glu Thr Val Val
1               5                   10                  15

Asn Arg Ile Ala Ala Gly Glu Val Ile Gln Arg Pro Ala Asn Ala Ile
            20                  25                  30

Lys Glu Met Ile Glu Asn Cys Leu Asp Ala Lys Ser Thr Ser Ile Gln
        35                  40                  45

Val Ile Val Lys Glu Gly Gly Leu Lys Leu Ile Gln Ile Gln Asp Asn
    50                  55                  60

Gly Thr Gly Ile Arg Lys Glu Asp Leu Asp Ile Val Cys Glu Arg Phe
65                  70                  75                  80

Thr Thr Ser Lys Leu Gln Ser Phe Glu Asp Leu Ala Ser Ile Ser Thr
                85                  90                  95

Tyr Gly Phe Arg Gly Glu Ala Leu Ala Ser Ile Ser His Val Ala His
            100                 105                 110

Val Thr Ile Thr Thr Lys Thr Ala Asp Gly Lys Cys Ala Tyr Arg Ala
        115                 120                 125

Ser Tyr Ser Asp Gly Lys Leu Lys Ala Pro Pro Lys Pro Cys Ala Gly
    130                 135                 140

Asn Gln Gly Thr Gln Ile Thr Val Glu Asp Leu Phe Tyr Asn Ile Ala
145                 150                 155                 160

Thr Arg Arg Lys Ala Leu Lys Asn Pro Ser Glu Glu Tyr Gly Lys Ile
                165                 170                 175

Leu Glu Val Val Gly Arg Tyr Ser Val His Asn Ala Gly Ile Ser Phe
            180                 185                 190

Ser Val Lys Lys Gln Gly Glu Thr Val Ala Asp Val Arg Thr Leu Pro
        195                 200                 205

Asn Ala Ser Thr Val Asp Asn Ile Arg Ser Ile Phe Gly Asn Ala Val
    210                 215                 220

Ser Arg Glu Leu Ile Glu Ile Gly Cys Glu Asp Lys Thr Leu Ala Phe
225                 230                 235                 240

Lys Met Asn Gly Tyr Ile Ser Asn Ala Asn Tyr Ser Val Lys Lys Cys
                245                 250                 255

Ile Phe Leu Leu Phe Ile Asn His Arg Leu Val Glu Ser Thr Ser Leu
            260                 265                 270

Arg Lys Ala Ile Glu Thr Val Tyr Ala Ala Tyr Leu Pro Lys Asn Thr
        275                 280                 285

His Pro Phe Leu Tyr Leu Ser Leu Glu Ile Ser Pro Gln Asn Val Asp
    290                 295                 300

Val Asn Val His Pro Thr Lys His Glu Val His Phe Leu His Glu Glu
305                 310                 315                 320

Ser Ile Leu Glu Arg Val Gln Gln His Ile Glu Ser Lys Leu Leu Gly
                325                 330                 335

Ser Asn Ser Ser Arg Met Tyr Phe Thr Gln Thr Leu Leu Pro Gly Leu
            340                 345                 350

Ala Gly Pro Ser Gly Glu Met Val Lys Ser Thr Thr Ser Leu Thr Ser
        355                 360                 365
```

-continued

Ser Ser Thr Ser Gly Ser Ser Asp Lys Val Tyr Ala His Gln Met Asp
    370                 375                 380

Arg Thr Asp Ser Arg Glu Gln Lys Leu Asp Ala Phe Leu Gln Pro Leu
385                 390                 395                 400

Ser Lys Pro Leu Ser Ser Gln Pro Gln Ala Ile Val Thr Glu Asp Lys
                405                 410                 415

Thr Asp Ile Ser Ser Gly Arg Ala Arg Gln Gln Asp Glu Glu Met Leu
            420                 425                 430

Glu Leu Pro Ala Pro Ala Glu Val Ala Ala Lys Asn Gln Ser Leu Glu
                435                 440                 445

Gly Asp Thr Thr Lys Gly Thr Ser Glu Met Ser Glu Lys Arg Gly Pro
450                 455                 460

Thr Ser Ser Asn Pro Arg Lys Arg His Arg Glu Asp Ser Asp Val Glu
465                 470                 475                 480

Met Val Glu Asp Asp Ser Arg Lys Glu Met Thr Ala Ala Cys Thr Pro
                485                 490                 495

Arg Arg Arg Ile Ile Asn Leu Thr Ser Val Leu Ser Leu Gln Glu Glu
                500                 505                 510

Ile Asn Glu Gln Gly His Glu Val Leu Arg Glu Met Leu His Asn His
            515                 520                 525

Ser Phe Val Gly Cys Val Asn Pro Gln Trp Ala Leu Ala Gln His Gln
            530                 535                 540

Thr Lys Leu Tyr Leu Leu Asn Thr Thr Lys Leu Ser Glu Glu Leu Phe
545                 550                 555                 560

Tyr Gln Ile Leu Ile Tyr Asp Phe Ala Asn Phe Gly Val Leu Arg Leu
                565                 570                 575

Ser Glu Pro Ala Pro Leu Phe Asp Leu Ala Met Leu Ala Leu Asp Ser
            580                 585                 590

Pro Glu Ser Gly Trp Thr Glu Asp Gly Pro Lys Glu Gly Leu Ala
            595                 600                 605

Glu Tyr Ile Val Glu Phe Leu Lys Lys Ala Glu Met Leu Ala Asp
            610                 615                 620

Tyr Phe Ser Leu Glu Ile Asp Glu Glu Gly Asn Leu Ile Gly Leu Pro
625                 630                 635                 640

Leu Leu Ile Asp Asn Tyr Val Pro Pro Leu Glu Gly Leu Pro Ile Phe
                645                 650                 655

Ile Leu Arg Leu Ala Thr Glu Val Asn Trp Asp Glu Glu Lys Glu Cys
                660                 665                 670

Phe Glu Ser Leu Ser Lys Glu Cys Ala Met Phe Tyr Ser Ile Arg Lys
                675                 680                 685

Gln Tyr Ile Ser Glu Glu Ser Thr Leu Ser Gly Gln Gln Ser Glu Val
            690                 695                 700

Pro Gly Ser Ile Pro Asn Ser Trp Lys Trp Thr Val Glu His Ile Val
705                 710                 715                 720

Tyr Lys Ala Leu Arg Ser His Ile Leu Pro Lys His Phe Thr Glu
                725                 730                 735

Asp Gly Asn Ile Leu Gln Leu Ala Asn Leu Pro Asp Leu Tyr Lys Val
            740                 745                 750

Phe Glu Arg Cys
            755

<210> SEQ ID NO 2
<211> LENGTH: 57497
<212> TYPE: DNA

<213> ORGANISM: Homo sapiens

<400> SEQUENCE: 2

| | |
|---|---|
| gaagagaccc agcaacccac agagttgaga aatttgactg gcattcaagc tgtccaatca | 60 |
| atagctgccg ctgaagggtg gggctggatg gcgtaagcta cagctgaagg aagaacgtga | 120 |
| gcacgaggca ctgaggtgat tggctgaagg cacttccgtt gagcatctag acgtttcctt | 180 |
| ggctcttctg gcgccaaaat gtcgttcgtg gcaggggtta ttcggcggct ggacgagaca | 240 |
| gtggtgaacc gcatcgcggc gggggaagtt atccagcggc cagctaatgc tatcaaagag | 300 |
| atgattgaga actggtacgg agggagtcga gccgggctca cttaagggct acgacttaac | 360 |
| gggccgcgtc actcaatggc gcggacacgc ctctttgccc gggcagaggc atgtacagcg | 420 |
| catgcccaca acgcggagg ccgccgggtt ccctgacgtg ccagtcaggc cttctccttt | 480 |
| tccgcagacc gtgtgtttct ttaccgctct cccccgagac cttttaaggg ttgtttggag | 540 |
| tgtaagtgga ggaatatacg tagtgttgtc ttaatggtac cgttaactaa gtaaggaagc | 600 |
| cacttaattt aaaattatgt atgcagaaca tgcgaagtta aaagatgtat aaaagcttaa | 660 |
| gatggggaga aaaaccttt ttcagagggt actgtgttac tgttttcttg cttttcattc | 720 |
| attccagaaa tcatctgttc acatccaaag gcacaattca ttttgagttt cttcaaaac | 780 |
| aaatcgtttg tagttttagg acaggctgat gcactttggg cttgacttct gattacccta | 840 |
| ttgttaaatt agtgacccct cttagtgttt tcctgtcctt tatttcggag gacgcacttc | 900 |
| gaagataccca gattttatgg gtcatccttg gattttgaag cttataactg tgacaaaaaa | 960 |
| tgtgaaggga agagatttga acatgtggaa ggaaaagtg agtgcagact ataaacttcc | 1020 |
| aaaaagacaa gcccaaaata cacctaaacg ttatgtcaga ttattttgtt aaaatcagtt | 1080 |
| gttagtgacg tccgtacgtt aatagaaaaa gaatgcttc agtttggagt ggtaggtttc | 1140 |
| tagagggatt tattgtgaaa gtataaacta ttcagggcaa tgggactgag agaacagtgg | 1200 |
| gtagaaagga ccactgaagg aaaggaagag aattggaagg tagatgaaag aaggagcaag | 1260 |
| aacctgggga tgttttttcc ttttcacttg taatagtagt aacagaagca atggcagact | 1320 |
| ggcttttgtt tctactgtgt tagaatgaat tgacaggaca actgggccta ttattgtact | 1380 |
| gtgccagaat actgtaaaac aaaactaaac atactagctt ggtggcttgt aattaattac | 1440 |
| ttaagtggag attttattt tttttttatt tttttttag acggagtctc actttgtcac | 1500 |
| ccaggctgga gtgcagtggc gcgatctcag ctgactgcaa cctcctcctc acaggttcaa | 1560 |
| gggagattct cctgcctcag cctcccgagt agctaggact ataggcatgt gccaccacac | 1620 |
| ctggctaatt ttgtattttt agtagagatg ggatttctcc atgttggtca ggctggtgtc | 1680 |
| aaaactctcg atctcaggtg aaccgcctgc ctcagccttc caaagtgctg ggattacagg | 1740 |
| cgtgagccac cgcgccctgc agttttttgt attttaata gagacagggt ttcaccatgt | 1800 |
| tagccaggat ggtctcgatt tcctgacctc aggtgatctg cccgctttgg cctcccaaag | 1860 |
| tgctgggatt acaagcatga gccaccgcgc ccggctcaag tggagatttt tatatggagt | 1920 |
| ccagttatac tcttttaat atataagttg agatgactaa tacaacttca atacaggggc | 1980 |
| tcatgagaaa tgtctgtaat atttaagtaa cttattgtct tctttctttt tttttaaga | 2040 |
| tgaagtctta ctctgttgcc caggcggaag tgcagtggcg tgatcttggc tcagggcaac | 2100 |
| ctctgcctcc tggtttcaag cgatcttcct gcctcagcct cccgagtagc tgggagtaca | 2160 |
| ggcgtgcatg accacacccg gctaatttt ttatttttag tagagacggg gtttctccat | 2220 |
| gttggccggg ctggtcttga actcctgacc tcaggtgatc cgcccacctc agcctcccca | 2280 |

```
agtgttggga ttacaggtgt gagcccccgt gcccagccta ttatcttatt tctgaataaa    2340
gaattgtctg tgtggggaat agataactct ttctcatgca gcccctgcta gaaaatttgt    2400
tttctctagc agttggtctg tgcttatagg ctactctttg aaagcacaaa aaatttattg    2460
acttcttttt tttgggtttt tttttttttt tgagacagag ttttgccctt gttgcccagg    2520
ttggagtgca atggcgcgat ctcagctcac cgcaacctcc acctcctggg ttcaagtgat    2580
tctcctgcct tagcctcctg agtagctggg attacaggca tgcgtcacca tgcctggcta    2640
attttgtatt tttagtacaa atggggtttc tccatgttgg tcaggctggt ctcaaactcc    2700
tgacctcagg tgatccaccc gccttggcct cccaaagtgc tgggattatg ggtgtgagcc    2760
attgcgcctg gccagaaaat tcattgactt cctaaagatt tattaacttt ctgcattact    2820 ttttttttc ccctccatcg taaatataaa agggaatagt agagaaaatc attcagaatt    2880
ttatttttta gtgacattat ttagtgacat tttattagag tcacttagga acctgaggct    2940
gaataaagtt caggtaaaag taaaattagt tgagaagaga catctgccaa aagaaatcta    3000
tttttaactt cacttgctgt ctttcctaga ggaacagaaa tagtgctgaa tgtcctatta    3060
gaaatgatgt tgctctgcc cgtctcttcc ctctctctca cacaatatgt aaactcatac    3120
agtgtatgag cctgtaagac aaaggaaaaa cacgttaatg aggcactatt gtttgtattt    3180
ggagtttgtt atcattgctt ggctcatatt aaaatatgta cattgagta gttgcagact    3240 gataaattat tttctgtttg atttgccagt ttagatgcaa aatccacaag tattcaagtg    3300
attgttaaag agggaggcct gaagttgatt cagatccaag acaatggcac cgggatcagg    3360
gtaagtaaaa cctcaaagta gcaggatgtt tgtgcgcttc atggaagagt caggacctt    3420 ctctgttctg gaactaggc ttttgcagat gggattttt cactgaaaaa ttcaacacca    3480
acaataaata tttattgagt acctattatt tgctgggcac tgttcagggg atgtgtcagt    3540
gaataaaata gattaaaatc tattctcttc tgatgcttac attatagtgg tgggagacaa    3600
aatgggtata ataaatatta tattagatag cattaagtgc tgtggagaaa actaaagcag    3660
ggaggaagat aggagtgtgc aagccagaaa ggttgcaatt aaattgagta gttcaggaag    3720
gcttcaatat ggatgtgata tttgagagac cggtggaagt caaggagcaa gttgtgaggc    3780
tatttaaagg tattcttggc ttacagaaca atatacgcaa agactattaa atggaagcat    3840
acctgacatg ttaaaggact atcaaggagg ccagtttgtc tagaggctga aaaggaaaga    3900
gtaataggag atgaggtctg agtgaaaaca cgtaaatcct tgtgggccaa ggtaaaatct    3960
ttagcttttt ttctgaatat ggtgggatac tgttagaggg ttttaagcag aggttacgtg    4020
gtgtggtgag tttttttttt ttaatccttt gtctttctgt gtggaaaata gcaggacagg    4080
gcagaagcag tctgtcctgc agactgcttg gtcgcagtag agatgtaaga agcagtgaga    4140
ttctgggtta attatggagg caaagttctc agaatttgct gatatagggt atgagagaaa    4200
gaggaatcag gaatgatttc aaggttttgg tctgctaaat ggaaggagtt gccatttact    4260
aagatgggaa agactatgaa agaagcagat tttcagagag atcagaagtt catttggggg    4320
catgttcaat ttaagatgcc tgttagttgg atgtttatgt gagtttggaa tgcagggtag    4380
agatttaggg atgaatattt ggtagttgtc tgcatttaa tggtattaaa agccacgaga    4440
aggatgggca tggtggctca cacctgtaat cccagcactt tgggaggcca aggcgggcag    4500
atcacctgag gtcgggagtt cgagaccagc ctgaccaaca tggagaaacc ccatctctac    4560
taaaaatata taattagccg ggcgtggtgg cacatgcctg taatcccagc tactcgggag    4620
```

```
gctgaggcag gagaatcgct tgaacctggg aggtggaggt tgcgatgagc cgagatcgca    4680
ccgttgcact ccagcttggg caacaagagc aaaactccat caaaaaaaaa aaaaaaaaa     4740 aaaaaaagcc ttgagactca cctgaaaaga tgctcaacat tattggtcat taggaaaatg    4800
aatgaaaacc acaatgagat accacttcac acctattagg atggctatta tcaaaaacaa    4860
aaacaagtgt ttgcaaggat gtagagattg gaattcttgt gtattgctag agggaatgta    4920
aaatagtgca gggtgctgtg gaaaatgctg tggtgattcc tcaaaaaatt aaacataatt    4980
atataatcca gtaattccac ttctgagtta ttcccaaaag aagggatgca agcagatatt    5040
tgtacactca tattcatggc agcattattt acagtagcca aaaggtgaaa gcaacctaag    5100
tgtccgtcag tggatgaatg gataaacaaa atggaataat ttcagcctta aatagaaata    5160
aaatgttgac acatgttgca acatatacga accttgaaga catcatgtta agttaaataa    5220
gttggtcact aaaggacaaa tattgtatga ttccccttat gaggttccta gagtagtcac    5280
attcatagag acagtagagt ggtggttgcc cagggccggg gggagcgagg agaatggaaa    5340
ttattgttta ttgggtacag agtttctgtt tggggaagat gaaaaaattc tggagatgga    5400
tcatgatgat agttaacaca gcagtgtgaa tatagttaat ggcacagaac tgtacattta    5460
aaaatggtta agatggaaaa ttttctgtta catatatttt actgcaattt ttttaaattt    5520
tattattata ctttaagttt tagggtacat gtgcacaaca tgcaggtttg ttacatatgt    5580
atacatgtgc catgttggtg tgctgcaccc attaagtcat catttagcat taggtatatc    5640
tcctaatgct atccctcccc cctcccccac cccacaacag tccccagtgt gtgatgttcc    5700
cctttctgtg tccatgtgtt ctcattgttc aattcccacc tatgagtgag cacatgcagt    5760
gtttggtttt ttgtccttgt gatagtttgc tgagaatgat ggtttccagc ttcatccatg    5820
tccctgcaaa ggacatgaac tcatcatttt ttgtggctgc atagtattcc atggtgtata    5880
tgtgccacct tttcttaatc cagtctatca ttgttggaca tttgggttgg ttccaagtct    5940
ttgctgttgc gaatagtgct gcagtaaaca tacgtgtgca tgtgtcttta tagcagcatg    6000
atttataatc ctttgggtat atacccagta atgggatggc tgggtcaaat ggtatttcta    6060
gttctagatc cctgaggaat tgccacactg acttccacaa tggttgaact agtttacagt    6120
cccaccaaca gtgtaaaagt gttcctattt ctccacatcc tctccagcac ctgttgtttc    6180
ctgacttttt aagatcgcca ttctaactgg tgtgagatgg tatctcattg tggttttgat    6240
ttgcatttct ctgatggcca gtgatgatga gcatttcttc atgtgttttt tggctgcata    6300
aatgtcttct ttcgagaagt gtctgttcat atccttcact cacttttga tggggttgtt     6360 tgttttttc ttgtaaattt gagttcattg aaaaattaga attttttttt ttttccctt       6420 tttagaggca aggtctcact ctgtcgccca cactggagtg cagtagtgta agcatagctc    6480
actgtaacct tgaactcctg ggctcaagca attctgtcat ctcagccagc tgaagtagta    6540
actgtaggtt cacaccacca tgcctatttt tgttttgta gaaatagggc cttgcttgt      6600 tgccaaggct ggtcttgaac tcctgacctc aagcagtcct cctgtctcag cctcccaaag    6660
tgctgggatt ataggtgtga gccactgcac ccagccttgg agatttttaa taaagaagct    6720
tgtcaattaa acaaacaaca aaaagccctg agactgaatg agataatcaa gagagtatgt    6780
gtagatagag aagaggtcca aggaaggagt cttgggtgac tctgatgtca agtgaggaca    6840
tgaggcagaa acagcagtga ctgagaagga gccacctagt aagaaaggag gaacaccagg    6900
acagtgtggt attctggatt ccaaacaagg aagttactgc taattttaaa gctcttctca    6960
ggctgggcat ggtggctcac acctgtagtc ccagcacttc gggaggctga ggtaggtaaa    7020
```

```
tcacttgagc tcatgtgttt gagaccagct tgggcaacat ggtgaaacct catctctact    7080
aaaaatataa gaaattaagg ccaggtgtgg tagttcatgc ctgtaatccc agtgctttgg    7140
gaggtcaagg cagccagatc atttgagatc aggagttcga gaccagcatg gccagcatag    7200
tgaagcccca tctctactaa aaatacaaga aaaaattaac caagcatggt ggcgcatacc    7260
tgtaatccca gccactctgg aggctgagac atgaaaattg cttgaacccg ggaggcggag    7320
gttgcagtga gctgagatct cgccactgca cttcagcctg ggtgacagag caagactctg    7380
tctcaaagga ggttgcagtg agctgagatc tcgccactgc acttcagcct gggtgacaga    7440
gcaagactct gtctcaaaaa aaaaaaaaac aaaaccaag aaaagaaaaa aaaactcttc    7500
taagaggatt ttttttttcct ggattaaatc aagaaatgg gaattcaaag agatttggaa    7560
aaatgagtaa catgattatt tactcatctt tttggtatct aacagaaaga agatctggat    7620
attgtatgtg aaaggttcac tactagtaaa ctgcagtcct ttgaggattt agccagtatt    7680
tctacctatg gctttcgagg tgaggtaagc taaagattca agaaatgtgt aaaatatcct    7740
cctgtgatga cattgtctgt catttgttag tatgtatttc tcaacataga taaataaggt    7800
ttggtacctt ttacttgtta aatgtatgca aatctgagca aacttaatga actttaactt    7860
tcaaagactg agaattgttc ataaataaac tattttaccct gcagagacct ctgatatatg    7920
tttcttgatg gaagtaccca gtaccaccta tgaagttttc ttgtcaaaaa atcaaatgtg    7980
aatctgatca ttacttagat ctaagtacca atatatgaaa aatataggag acaaggaagc    8040
atggtaaatg atactgagat tgggagacta catggaaaaa gacttgttcc cttcaacaga    8100
tagacagcag ggaaaaaaga atagagaaag gagtaaagaa cctgtagatt aaaagacatt    8160
taagggacat atgaaccagg tccagtgtat agatcttacc taaatcctga tggagcaaac    8220
tataaaaaaa ttttttttgag acaaatgttt gaatacaggt tgactatttg atggcattaa    8280
ggagaaatta tgaattatct tggtataaga atattgtcat gggttttttt ttttgagtcc    8340
ttacctgtta agatacatac taaaatattt gtgggtaaaa ttatatgacg tataggagta    8400
tatgatttag aaaacggatt aaaatataaa aggataaaat aggatcttat attttgtgac    8460
tcacttcctg ttggatatct ttctacccag taaaatatagt cctatctagg ttttaatggc    8520
tacatgtatg tactgtagtt tgtttaaatg gtttcctatt gaacatttat gctctttgcc    8580
attttttcct gtttaacgtt ctgttttttt tttttgttttt tttttttttt gagacagtct    8640
tgctctgtta ccagactgg agtgcagtga catgatctca gctcactgca acctctgcct    8700
tctgggttca agctattctc ctgcctcagc ctcctgaata gctgtgatta caggcgtgca    8760
ccactatgcc cagctaattt ttgtattttg ggtagagaca gggtttggcc atgttggcca    8820
ggctggtctt gaactcctga ccttgaatga tctgcccgcc ttggccttgc aaagtgctgg    8880 gttacaggc atgagccacc acgtctggcc ttgtttaagg tcctgatgag tattcttata    8940
ggtacactgt gtttcgttta attatttcct taggataaat ttatagaaat aacattcctt    9000
ggtaaaagaa tacatatttt aaaaactgta ttagtttcct gttgctgtca aaaaatttcc    9060
agaaacttag tggcattaaa caatacaaat taattattct acagttctgg agatcagaag    9120
atacgggtct tactaggcct cactaggcta aaatcaaggt tttggcaggg ctgtgttcct    9180
ctatggaggt tccaagggac cagagaaact actttacagt agttatttta agggaatgaa    9240
agtgaagatg gggttgggca gtcaaagagg ctgttacttt tcatttttgg cctttcagta    9300
gtttgaattt ttttatcata tacatgtatt actttaattt ttaaaaagta aaaagcagct    9360
```

```
gtgattcagt ctctgtaatt tagatcaatt tacatcaaac tagggtggtc tcatgtgttg    9420
tcttgctcac agtgaccact agattattcc aagaagggac aatttccaag acttggttta    9480
cactgagacg gctcctgatt ttaaggatac cttagatcaa actctaggaa ggcagtttca    9540
ttttggcctt gcagttccct gggtcatttt ccaagcccat ggcctcctgg agtcttcgcc    9600
tagctgtagg ttatctttgt ggctattatt tcactgtaat tatacaggaa gatttattga    9660
gggatttctg tgtaccagcc gtggttctca gcactttgta tactttgtat taactctgac    9720
tcctgacagt aactctacag aggttctgct gttacccagt tttacataga aacatggcca    9780
gcggacgcag ttagaaaatg gcaaagtggg gattagaaac taggcagttt gactccagag    9840
tctgtgcccc tgtccacttg gctccactgc tggggaagag gcctctgaag cagcaggacc    9900
atctgctgtg ccgtgtgtag tggtactcta tcttcctggt gtgatgttgt gttctacttt    9960
gcattttcat gtctttcctt atacaggtct caaaatcatt tactttttt tttttttttt    10020 tgagacggag tctcactctg ttgcccaggc tagagtgtag tggcatagtc tcactcactg    10080
caacctccgc ctccgaggtt caagtaattc tcctgcctca gcctcccaag tagctcggat    10140
tacaggcaca tgccaccaca gctagcaaat ttttgtattt ttagtagaga ttggtgtttc    10200
accatgttgg ccaggctgtt cttgaactcc tgacctcagg tgatccaccc acctaggcct    10260
cccaaagtgc tgggattaca ggcgtgagcc accccaccca gccttatatt ttttaatgat    10320
gcacattagc tcaattacat aaaccaggga aatccagcta ggacctggtg atttctgagc    10380
ctgacccatg tgactttcaa tgaactgaac ttgccacagc tgtatttact gtctactgag    10440
atgctgtcac acagacccg tcatagcaca gttcctgagt tacatcttta catactgtag    10500
tatccttctt gtgaaaaag atacagattc caaaggtctg agaaaccaat cttggttata    10560
aaggggaaaa atggtcatgg gttttaaaa tttgttttgt cttaattgca tttcaaattt    10620
acatttctaa atgaataatt gcttatataa agcagttttg attaacaata taaaacacta    10680
tctatttgga gtgattcctt tacccatttc tgaaggcaag ttttaaaaat tactagaaga    10740
cacttcattg agaatattat taaacatgcc tatagttcta ccacctcaac acaattgctt    10800
attaacacat taatgttttg gtgtgttttg gacttttttaa tatgtatttt tcacttgttc    10860
tagtaattat gctacagatt gatcatttct ttttcaacat gtcatcaaag caagtgagca    10920
aagtgctcat cgttgccaca tattaataca aaatggaagc agcagttcag ataacctttc    10980
cctttggtga ggtgacagtg ggtgacccag cagtgagttt ttctttcagt ctattttctt    11040
ttcttcctta ggctttggcc agcataagcc atgtggctca tgttactatt acaacgaaaa    11100
cagctgatgg aaagtgtgca tacaggtata gtgctgactt cttttactca tatatattca    11160
ttctgaaatg tatttttgc ctaggtctca gagtaatcct gtctcaacac cagtgttatc    11220
ttttttggca gagatcttga gtacgttttc ttttctcctt attgataaat tgataatcct    11280
caaggatgat tattaggtga tactcttact tcatggattc ttaaaagata tgatttaaca    11340
tattacaagt gcctagcaag gtgtctgtta cacgtaggta ttttaagtaa atggtagctg    11400
ctgatgtaat ttctgcccct ttgcccttca gttggggtat tgctttggac cgattagagg    11460
gctgtggctg ggatgctaaa ggttcatgtt tccttagctg gctcctgagc caccagctcc    11520
caccacctgt gtatacctgt gctagtttgc cttccacaa gtagctgctg gtatctgtt    11580 atgctggtac agttttcaga aactgatgaa tggcctttga acagaacaaa atgagattc    11640 agaataacaa aattgcacct tgttttat aagcactggc cattcactag ttgaagactg    11700
gtaggaatac ctaattcatg ccaaaagaaa gataatttt aaaaatcaca caggttgttt    11760
```

```
gtagattaaa agggaaaata ggctaggtat agtggctttg cctgtgagtt tgggaggctg   11820
aagtgggagg attgcttgaa gtcaggagtt tgagaccagc ctgggaaaca gagcaagacc   11880
ccgtctctac agaaaatttt taaaaaatta gctgggcatg gtgatgcata tctgtagtct   11940
tagctactcc ggaggtggga agattgcttg agcccagcag tttgaggctg cagtgagctg   12000
tgattacacc actgtactcc aaccttaaaa taaataaata aataagggaa aatatcttca   12060
acaaaggata gttctgtctg tttctcagtc ttcctcaaca gataaatgtg tgaagtaatg   12120
gaaggtggag atttcagatt acacaacatt aatgctaagg gcgtttgact ctgtgtgaat   12180
tctaattgcc ctagatctag acgggctgat actattagaa tcccctgtca ctaactgaag   12240
acagagttgt aagttaatgc cttcctagat agcctagatt gtggtatgct gctgcatgct   12300
aaaatggctc cccttccata gcaggatgaa atagagtcat tatcttggca accagcccct   12360
gccaatgtgc tctcagtctg cctttccagc cccttctctc tacctattcc cagctgccat   12420
gtattctaaa gcctctatgc tttcattttt gttttttgcct tcctggatgg tcttttcctgc   12480 tgtctccacc tgaaactatt cctctctaaa gaacagatga attgccatct ctctgggatg   12540
cttttaccca ccctcactcc cacctcaggc tgaatggacc cttctctaga tcgcttagca   12600
tattgttcta cagttaggta aaagtctac ctatcactag atcaagagct ttgttttttt   12660
ttattaattt aattttcttt tttttttttc tttttttttt gagacagagt ctcgctctgt   12720
cgcccaggct ggagtgcagt gcacaatctt ggctcactgc aagctccgcc tcccaggttc   12780
acaccattct cctgcctcag cctcccgagt agccgggact acaggcgccc accaccacgc   12840
ccagctaatt ttttgtattt ttagtagaga cggggtttca ccatgttagt tagccaggat   12900
ggtctcgatc tcctgacctc gtgatccacc cacctcggcc tcccaaagca ctgggattac   12960
aggcatgagc caccgcgccg agccccaaga ccttcttta ttaccagggc ttccacagac   13020
ctgacacatg gtagttcctc aataaataat tgcagaatta ctgaaaaatt ttactgttaa   13080
cttaggcagt ggtaaaacca ttgtttggta gctcagaact cagcaagtaa atagcaacat   13140
ttgctggaag aacagatagt tttcaaatc caattcaagg actgggtatg gtggctcatg   13200
cctgtaatcc cagcactttg ggaggccgag gcaggcgtat ccaggagttc gagactagcc   13260
tgaccaacat ggtgaaactc cgtctctact aaaaatacaa aattagccag gtgtggtggt   13320
gggcacctgt aatctcagct acttgggagg ctgaggcagg agaatcgctt gaacctggta   13380
ggcggaggtt gtagtgagct gagattgtgc cattgctctc cagcctggga acaagagca   13440 aaactccgtc tcaaaaaaaa aaaaaatcca attcaaatga ttatgaagt agtggagaaa   13500 taaacaggaa aatgataaat aattaagata atatataata tggctatatt ttaatctatt   13560
gttgatatga ttttctcttt tccccttggg attagtatct atctctctac tggatattaa   13620
tttgttatat tttctcatta gagcaagtta ctcagatgga aaactgaaag ccctcctaa   13680 accatgtgct ggcaatcaag ggacccagat cacggtaaga atggtacatg ggagagtaaa   13740
ttgttgaagc tttgtttgta taaatattgg aataaaaat aaaattgctt ctaagttttc   13800
agggtaataa taaatgaat ttgcactagt taatggaggt cccaagatat cctctaagca   13860
agataaatga ctattggctt ttgtggcatg gcagcctgcc acgtccttgt cttttttaag   13920
ggctaggaga ttctttattg ggatggcaaa agtcaatggc agggtagttg tcattgaaag   13980
aagattaagc ttgaccccag aaggcatggg ttagagccca gccttgtcac tcaatggttg   14040
tatgtccaga ggcaagtcac ttaacatccc ttaaccccag ttttctcatc tgtcaaatga   14100
```

```
agcaaagaat acttgccctc ttgacttaaa gggtgtctga tgagacatat gactgtatca   14160
ttagctggga gaaagtccat cgtgctgcct atgtatagtg cctcaagttg gtctctttcc   14220
cttctatgat tacacaaagc actccgctgt catgttatcc atcccgcccc tccattccaa   14280
gtcccatcta gagcacatct tcttgaagtc cactgtaacc tgcctaatcc tggatgtgac   14340
gagccaggca ggaggcagaa aagaatgtgt gttttgcaat acatgttaag agacatcttg   14400
ggctgggcac ggtggctcac acctgtaatc tcagcacttt gggaggctga ggagggcgga   14460
tcatctgagg ttgggagttc gagaccagcc tgaccaacat ggagaaaccc catctctact   14520
aaaaatacaa aattagccag cgtgatggc gcatgcctgt aatcccagct actcaggaag   14580
gctgaggcag gagaattgct tgaacccggg aggcagaggt tgtggtgagt tgagatcatg   14640
ccactgcact ccagcctggg caacaagagt gaaacagggt ctcaaaaaca aaacaaaca   14700 aacaaaaaaa atcttttacc acggtgacca ccatgtgatt tccaagaact tcaaatgatc   14760
taagaaattt tgtgattatt actagtttga aaaatacttt tttttttttt gagacaaagt   14820
ctcactctgt tgcccaggct gaagtgcagt ggtgtgatct cagctcactg caatcactac   14880
ctcttgagtt caagcagttg tcctgcctca gcctcttgag tacctgggat tacaggcatg   14940
cgtcaccatg cccggctaat ttttgtattt ttagtagaga cagggtttca ccatgttggc   15000
caggctggtc tcgaactcct gacctcaggt gacccaccca ccttggcctc ccaaagttct   15060
gggattacag acgtgagcca ctgcacccag cctgaaaaat atctttgaat gccatgtgat   15120
actatacttg tcagtttaca tgtgtgtccc actaaatcat gtactctcct gagcaggatc   15180
atgctttgtc ttcatatttt ctgtacaaag caaagactct gacacaaagc tagccccag   15240 tgcatagttg agaaatcagt gaatgaatgt gggaggcagg aaaaatgtcc tttaattctt   15300
ctgttaatgc tgtcttatcc ctggcccag tcagtgctta gaactgtgct gttggtaaat   15360
ataattggat tcactatctt aagacctcgc ttttgccagg acatcttggg ttttatttc   15420 aagtacttct atgaatttac aagaaaaatc aatcttctgt tcaggtggag gaccttttt   15480 acaacatagc cacgaggaga aaagctttaa aaaatccaag tgaagaatat gggaaaattt   15540
tggaagttgt tggcaggtac agtccaaaat ctgggagtgg gtctctgaga tttgtcatca   15600
aagtaatgtg ttctagtgct catacattga acagttgctg agctagatgg tgaaaagtaa   15660
aactagctta cagatagttt ctggtcaagg tttagccacc aattttgcag tttctctcat   15720
ctccccagga aagagcagtt ggtctttaga tcaatgagag ctcttttatg gcagacaaaa   15780
caaagtgact ctagccaact tgagctaaaa agaaatttag tggaaggcta ggagttacca   15840
catgaagtgt gtgcagctgc cccttggaga gaataagaac cagggtgcct ctgggactta   15900
acatcattac tgtactccag ttgttttcat tcttttcctg actttgctct agagtcagtt   15960
tcctaacaga gtacattcga tgatcatgtg cccatatctg tggggagaag atttcttgat   16020
tggcagtctt actaagggtg catatcaagt agaatggaat agaggtagtt tcctaaagga   16080
agatgagagg ctgttaccag gaggaggaga agggattcag gacagatgaa aacaacgtta   16140
tatccatgat agacttacgc tgctggtaca gatggtacag gtggcttcag tataggctct   16200
ccgaacccac atatcattga ttatgatagg gatatgttaa ctattttca gtgtatatat   16260 gtatatgtgt gtgtgtatat atatgtatat gtatatatat atgtatgtgt atatatgtat   16320
atgtatatat ttatatatgt atatgtatat atttatatat gtatatgtat atatttatat   16380
atgtatatgt atatatattt atatatgtat atgtgtatat atatatattt atatatatgt   16440
atatgtgtgt atatatatat attttttttt gaaacggaat ttcgctcttg ttgcccaggc   16500
```

```
tggagtgcaa tggtgcgatc tcagctcact gcaacctctg cctcctgggt tcaagcgatt    16560
ctcctgtctc agcctcccga gtagctggga ttacaggcac ttgccaccat gcccggcaat    16620 ttttttttg ttttttttta gtagagaggg ggtttaatca ttttggccag gctggtcttg     16680
aactcctgac ctcaggtgat ctgcctgcct tggcctccta aagtgctggg attacaggcg    16740
tgagccacca tgcctggcca ttttcagta tttctttttt tttttttttt tttttttttt     16800
ttgagacaga gtttcactct tgttgcacag gctggagtac aatggtgtga tctcggctca    16860
ccgcaacctc tacttcccag gttcaagcaa ttcgcctgcc tcagccttct caagtagctg    16920
ggattacagg catatgccac catgcccggc taattttgtg tttttagtag agatgggtt     16980 tctccatgtt ggtcaggcta gtctcaaact cccgacctca gatgatcctc ccgccttggc    17040
ctcccagagt gctgggatta ctggcatgag ccagcgctcc tggcccattt ttcagtattt    17100
ctaaaaaaaa tctaaagtgg gtcaaacatt tcaccttaat agaatgacag gtttgtacat    17160
caagtttctt tgcttttct tggaatttta tactttttt ttttttttgg agacagagtc      17220
ttgctgtgtt acccaggctg gagtgcagtg gtgcgatctc agctcaccac aacctccacc    17280
tccaggttga gcaattctc ctacctcagc ctcctgagta gctgggatta caggcacatg     17340
ccaccacacc cggctaattt ttttttttt tttgtatttt tagtagagac agggtttcac     17400
catgttgtcc aggctggtct cgaactcctg acctcaggtg atccgcccat ctcggcccac    17460
caaagtgctg ggattacagg cgtgagccac tgcacccggc cttttcttg gaatttttatc    17520 aatcagtgtc agaatattca ttacctccta aaaataaagg agttctagtt ggctgttttg    17580
attctaggtg tggtaaagtg aaatattgtt acttaataaa tgcattttgc tagacacaat    17640
ccttcggttc acgagctctg tagagaaaag agaaataacc gccaaccaag aaaagattgg    17700
gagatactag aataagaccc aggggcagga agaagccagt gagaaggagg gcatgttgag    17760
agctctgaga gagaataaaa gcaggggttg ttggagctag cttctcaaga tgtccttgag    17820
gcaaaccaga cctttgggac actctgaaaa taaaactgaa agtgaagaga ttgtgggccg    17880
aatgtggtgg ctcacgcctg taatcccagc actttgggag gtcgaggcgg gtggatcacc    17940
tgagatcagg agttcgatac cagcctggcc aacatggcga acgccatctc tactaaaaaa    18000
tacaaaaaaa attagctggg cctggtggca ggcgcctata atcccagcta ctcgggaggc    18060
tgaggcggga gaatcgcttg agtccaggag gcggaggttg cagtgagctg agatcgtgcc    18120
attgcactcc agcctgggca acaagagcaa aactctgtct caaaaataaa taaaaataaa    18180
taaaaaagag atagtggcgt gatatccttg attctatcag caacctataa agtagagag    18240 gagtctgtgt tttgattcag tcacctttag cattttatt tccatgaagt ttctgctggt     18300 ttattttct gtgggtaaaa tattaatagg ctgtatggag atattttct ttatatgtac      18360 ctttgtttag attactcaac tccactaatt tatttaacta aaggggggct ctgacatcta    18420
gtgtgtgttt ttggcaactc ttttcttact cttttgtttt tcttttccag gtattcagta   18480
cacaatgcag gcattagttt ctcagttaaa aaagtaagtt cttggtttat ggggggatggt  18540 tttgttttat gaaagaaaaa aaggggattt ttaatagttt gctggtggag ataaggttat   18600
gatgtttcag tctcagccat gagacaataa atccttgtgt cttctgctgt ttgtttatca   18660
gcaaggagag acagtagctg atgttaggac actacccaat gcctcaaccg tggacaatat   18720
tcgctccatc tttggaaatg ctgttagtcg gtatgtcgat aacctatata aaaaaatctt   18780
ttacatttat tatcttggtt tatcattcca tcacattatt ttggaaccct tcaagatatt    18840
```

```
atgtgtgtta agagtttgct ttagtcaaat acacaggctt gttttatgct tcagatttgt   18900
taatggagtt cttatttcac gtaatcaaca ctttctaggt gtatgtaatc tcctagattc   18960
tgtggcgtga atcatgtgtt ctttcaaggt cttagtcttg aaaatattta tagtgtagta   19020
gaactatttt atcctccaat gctccttctt ttccttgtat ttccattatc atcactttag   19080
gatttcactt atttatcatt caacatttat taattgcctc tcatattcca ggctttgtgc   19140
tagaagttag ggatataaag acaaataaga tatttcctgc ccttaaagac tagattcgtg   19200
ttgctaagtc ttcattatca agaaaagcat aagtggggaa aagtgcttgc attatggatt   19260
cctcatagtt gctcccctct gcatgtaaaa atcaccattt ccatcataga ttcctagcgg   19320
tctcaggact ttataaagcc caaagtgcct atgtcataat atgaggaaaa atactgagac   19380
ccttccatat atgggaggta tatgatgag acagctcctg acttcacttt tcccagaaat   19440
ctgaaaagca gcagcagtca ttccagagcc cagtttctac tttgaagggc agattattta   19500
ttctttgagc taacctgact gaggaacaat tagtttgctt ttaatttact attttctttt   19560
tcttttcttt tctttttga gacagagtct cactctgttg cctaggctgg agtgcagtgg   19620
ctcaaacttg gctcactgca agctccgcct cccgggttca cgccattctc ctgcctcagc   19680
ctcccgagta gctgggacta caggcgcctg tcaccacacc cagctaattt tttgtatttt   19740
ttagtagaga cggggtttca tcgtgttagc caggatgatc tcgatctcca gacctcgtga   19800
tccacccacc tcggcctccc aaagtgctgg gattacaggc gtgagccacc gtgcccagcc   19860
actattttct ttctaattgt taatgaatta atttttttaaa actgtgctcc tagagcgaag   19920
ggagagctct gtttacagtg taacttttca gagcttcttt aactagattt taagatcaga   19980
attagttgtt gtgaaatctt agggactgta caagattaga aatcctctat agcagcattt   20040
cccaaagcag gcttccagaa cactagcctc atgaggcatt tgggaaaaa agagtttgct   20100 ggttcagtgt gtatgggcag tgccacaagc cgtaccctcc gttgaagaca ctcattccac   20160
acattactgc ataaaaagct tccaccagcc attcggcaaa cttattgagt gtctgctatt   20220
tcctgggtat tgtgctatat ggtagggtta tagtagtgaa caaagaagaa atgatgcctg   20280
ctctcagctg actttgcagt tggaaagaca catgaaataa ttacgccatt cattagcaga   20340
ttgtgctaga tgcctcactg gaaaaataaa ggacatgatg gaaaactctg tagggtcaga   20400
gaaagggatc attagagaag gttctttgaa gaaatatttt ttgaaatatg aaggataaat   20460
aggaattaac taggtaccaa taggttagga gtagagcttt ccagacagag ggactagttc   20520
ttgggaaggt ctccagacag aaataagtgt ggcttgtctg aggacctctt attcgcctat   20580
taaccttccc tccccagtaa acactcctgg gaacaacaca cattgtagaa ccacgttgtg   20640
gtgctgttca gtatagcaag taattcagca gagataagtt cttggaatct catctttggg   20700
atttagttac taagatacat tcaagtttga gcaaataag gtctcagagc ttggattcat   20760
tgttctgttc cagcaattag agcagtacct ggcacatagc acaagtgctt gaaaacactg   20820
actgagtagg gtaggtgggt gagtgggtgg gtgggtgggt gggtggatgg atggatggga   20880
ggatgggtgg gtgaatgggt gaacagacaa atggatggat gaatggacag gcacaggagg   20940
acctcaaatg gaccaagtct tcggggccct catttcacaa agttagttta tgggaaggaa   21000
ccttgtgttt ttaaattctg attcttttgt aatgtttgag ttttgagtat tttcaaaagc   21060
ttcagaatct cttttctaat agagaactga tagaaattgg atgtgaggat aaaaccctag   21120
ccttcaaaat gaatggttac atatccaatg caaactactc agtgaagaag tgcatcttct   21180
tactcttcat caaccgtaag ttaaaaagaa ccacatggga aatccactca caggaaacac   21240
```

```
ccacagggaa ttttatggga ccatggaaaa atttctgatc cataggtttg attaaacatg   21300
gagaaacctc atggcaaagt ttggttttat tgggaagcat gtataatttt tgtcctaagt   21360
ctgtgctcag ccctcccaca tgtgctcatt gctggttgac tgttggagtc tggttcttac   21420
ctctaagagg aagcccagga gagggcataa agccagcaca ctgtcctcac ctgatggtgt   21480
cagagtcctt acgagtaagc cctagccaga acattgctgg aagagatcaa gggccactgt   21540
ttgaaattgc acagcaggat acggaaaagg ggtaccttag gtataggcat tgtcattaaa   21600
gaaattgcta agatacttga gattttcctg tttaaggaat gagctttatg atacaaagag   21660
cagttctaaa aattagggag ggaattaact aaattaatta ggatatttct caaattcctt   21720
tacagttttt gtctctctgc tgatatagtg tttacatgat tgttatttac taaacaaatg   21780
ctattttgta ttgtgctcct tataacttaa ttgtttatta caaggttttg atggtgacct   21840
accaacaaca agtaatccca aacacagtct gaattttttg ttttccatcc agaaataaga   21900
tgaatctttc catttccgtg ttttcagttt tcatcatttt tatcctatag gttacttatc   21960 tttatttttaa agcatttcat aataatttta tagttttttgt tttgtttgct gtttgctgt   22020 tggaaatgga atattccctc cttccatttta gactgctaac cagctgtaaa tgtttcaaaa   22080
tatgcatgtt ttacagcagt tgttcaaagc aatacaggaa cagtaaggac agagccagtc   22140
attttacaac cacattctgt taaactgatg tctattagca gggttttttcc tattttatta   22200 ggaaggactt acacctgata tataacaaag cttgttttaa tcaaggctca gaaaatgttt   22260
ttcattagtt ttttttcctaa ccatgaagaa taactgcttt gtaacacaca tgctggctat   22320
aaagcagaca aaaaattcac tgtaggtgct gcctgactgg cctctgtccg tgtttctgtt   22380
ggggctgctt accacagcct ctgcattatc attagctagt gtgttcacaa taccaagttc   22440
ccagtagcaa agaaaggtca agctcttacg catgccattc atttatctac actgtgcagg   22500
cgcactcagg tggcagggac aaagaccact cctttggcgc atctcaagtt cagaattctc   22560
agtagagggg ctccagctgt ccttttgtca ggtgcccatg cctgctccag gctgtgtgg   22620 tcaggacacg tgttacagag tacagtgaca ttaatgatgg ggccatggat atggtcagca   22680
ctcagaggat gttagtctct tcattgataa agtcacaacc acttttcctg ttggaaataa   22740
aaagatttga cgtatccttg tctacagcaa cacaggacaa cagataatca gcaggtcatc   22800
taaatctgtt cagagagaaa ggagagctgt ttcctgaaaa tacatcttcc cctgatttta   22860
gtcttatttt tttctgcctt tattgctttc taccctcttc aaaccagcct catttcctaa   22920
attaccttga atatgcattg acacttgtac tgcctgaaat tctggaaaac tcagtatggc   22980
tactccaccg tcagaacttc ctgagcaaag ttagttgctc tctcggctca ctgttttgtt   23040 ttgtttttgtt ttcctgcctc aggtttattt gtacaaatag cacaggagga ccagccccat   23100
gcagatggta gcccagggc ggggtaggg ggtcacacca gtccttctgt cctcatgttg   23160
gcagagatat ctactctgaa gcctttgtag gggcctgggc acctttggga gcctgagctg   23220
gaactgaagg tggagctgca gcctgggcct tggtttgatc cttggccttg gcctttggcc   23280
ggcacagcct gagcccctttg gcaatacggg cacgagcacg cttcccaagc ttgggatggg   23340
caatgtaggc aagtcgatcg agcttgcggc tgacacccctt tgggatcttg ggcttaacct   23400
ccttgggctt tacgagggcc ttgatagcct cggcacgtgc actcatggcc ttggcattgt   23460
tggcctgcat cttctttagg cccttcttgt tgtgcttctt ggcaaagtgc atgttcctca   23520
ggaacttggg gtccacccccc ttaagagatt cgtatctttg tgatcggggt ttcttgatac   23580
```

```
catttctgtg ccattttcgg gactggttgt gtgtggtgtg gttcttggac ttcgccatgt    23640 ctacaccttta agccgcggct cccgaagcac ctagaaccgg aagagttggc tcactattta    23700
gcacacacac acgtctataa tagtgctggc cacttggggt tggaattagt ttatttatca    23760
gcatgttgtc tcccagcact tggtgtgtgt gatatgcagt atgtatttgc agaatgaaaa    23820
gtctgagggc tgacatcata tttcccactg tgcccagaaa gagcacagtt agtccacatg    23880
agctaatggg ggcaaaggga agtgaggagg gagaatgtac tgccttatca tgttttctat    23940
tacttggctg aagtaaaaca gtcccaagcc gatagtaaga tagtgggctg gaaagtggcg    24000
acaggtaaag gtgcacctttt cttcctgggg atgtgatgtg catatcacta cagaaatgtc    24060
tttcctgagg tgatttcatg actttgtgtg aatgtacacc tgtgacctca ccctcagga    24120 cagttttgaa ctggttgctt tctttttatt gtttagatcg tctggtagaa tcaacttcct    24180
tgagaaaagc catagaaaca gtgtatgcag cctatttgcc caaaaacaca cacccattcc    24240
tgtacctcag gtaatgtagc accaaactcc tcaaccaaga ctcacaagga acagatgttc    24300
tatcaggctc tcctctttga aagagatgag catgctaata gtacaatcag agtgaatccc    24360
atacaccact ggcaaaagga tgttctgtcc cttcttacag gtacaaggca cagttttcct    24420
tcatttattc actaatttag cagaacctca ctaagagcct cctatatgcc aggctctgcg    24480
ttagcaataa aaggaatgcc atgcctcacc ccatcaggag gtgctgatag cttgtaggcg    24540
gagtggaaac agatgtgctc tagaggctct aaatattact tctgctgggg tcagttggga    24600
agccacaaca gctactgttc atcttccata aaagacaatc agccgggcac agtggctcac    24660
acctgtaaat cccagcactt tgggaggctg aggtgggtgg atcacaaggt caggtgtttg    24720
agaccagcct ggccaacgtg gcgaaaccct gtctctacta aaaatacaaa aattagccag    24780
gcatggtggc gggcgcctgt agtcccagct actcggagg ctgaggcagg agaatcgctt    24840
gaacctagga ggtggaggtt gcagtgagct gagactgtac cactgcactc cagcctgggc    24900
gacagagcga gactccatct caaaaaaaaa aaaaaaaaga ctgggttctg ttctgtggag    24960
gttcttgtct taacatatcc actgttgatt gcccagatgt tgatgtaatt aatttagcag    25020
tcgtaaatag tttagcactt gcattaaata gaccaaaccc catagtaggt atttgaaata    25080
cagaataaat gtgaggtacc cctgctctaa aggagtttat agtccagagc tgacttatgg    25140
aggatttctt tctattattt ctgggtctgc tactaatttg tctatttcat atcctaatta    25200
tccttgtttt cattttgatt gaaagggga gagcatagaa attgtggtaa aaggtagttt    25260
tattttttat ttgagatgga gtcttgctct gtcacccagg ctggagtgca gtggcacaat    25320
ctcatctcat tgcaacctcc acctcccgcg ttcaagcaat tctcctgcct cagcctcccg    25380
agtagctggg attacaggtg tgcaccacca cgcccagcta ttttttgtat ttttagtaga    25440
gatggatttt accatgttgg ccagtctggt cttgaactcc cgacctcagg tgatcctctc    25500
actttggcct cccaaagtgt taggattaca ggcctcagcc actgcaccca gcctaaagtt    25560
agttttagat taagtgtttt catgttttcc cttgcaaagt aataaactgg tcaagttatc    25620
accttgttcc atctccatat taatcagggt ccaaacagga gatagaaacc atgcaacaat    25680
ttgagtagtt gaataaagaa ttataaacag gagattagag taataggga ttagatagta    25740 agaggtgaag agataggaac agcagatata aagaacaacc atttcctcct atggctgaga    25800
taccatcccc tcaccacact ccccccaccta ctcactgaga tgcagacctt attgaagaga    25860
atgtaactgg cttgctgcga ggtaaagtca atgaggcgct ccccagtacc actctgaggg    25920
gatgctgggg aaaactgccc atgagaagag ggcacatgct gctggccact tgtgctaaag    25980
```

```
aacttgaagt ctgataggag tgcaccctaa cctggcatag aaaccctttc ttcctgctga    26040
gtccctctag caccttatac tggcaaagct ttacattgca aacctccatt atcacagagc    26100
aagcaatgaa agatggactc agagctgagg cgataaattg atagctagca tagcctctaa    26160
actgactttt atgactacat tttatggata gaaagtgttc ttatatatat tgtttcttta    26220
cataataggg gacttattca tggctgcaga tgagaaaaca gatcctaaga agttaagtga    26280
cttgcccaag gtcacacaaa gaattccact agttctaaaa tgacagtaat tacagttaac    26340
atacattgta tgtggcagat acatataaag cacatggcat taattttttt ttttgagatg    26400
gagtcttgct ctgtcgccaa gctggagtgc agtggcacga tctcggctta ctgcaacctc    26460
tgactccctg gttgaaggga ttctcctccc tcagcctccc gagtacctgg gattacaggc    26520
atgcgccacc acgcccagct aattttttgta ttttagtag acgtggtt tcatcatgtt      26580 ggccaggatg gtctcgatct cctgaccttg tgatccaccc gcctcggcct ccccaaatgc    26640
tgggattaca ggcgtgagcc accacgcccg gccacttggc atgaatttaa ttcccgccat    26700
aaacctgtga gataggtaat tctgttatat ccactttaca aatgaagaga ctgaggcaaa    26760
gaaagatgat gtaacttacg caaagctaca cagctcttaa gtagcagtgc caatatttga    26820
acacactcag actcgatcct gaggttttga ccactgtgtc atctggcctc aaatcttctg    26880
gccaccacat acaccatgtg tgggcttttt ctcccctcc cactatctaa ggtaattgtt      26940
ctctcttatt ttcctgacag tttagaaatc agtccccaga atgtggatgt taatgtgcac    27000
cccacaaagc atgaagttca cttcctgcac gaggagagca tcctggagcg ggtgcagcag    27060
cacatcgaga gcaagctcct gggctccaat tcctccagga tgtacttcac ccaggtcagg    27120
gcgcttctca tccagctact tctctggggc ctttgaaatg tgcccggcca gacgtgagag    27180
cccagatttt tgcctgttat ttaggaactt tctttgcaag tattacctgg atagttttaa    27240
cattttcttc tttgaaccta gttataaagg tattgtgctg ttgttcctag gcttagagtc    27300
ataaggcctg agctcacttc ctcactttgc ctccatctgg aaccttagac caacttccta    27360
ggaaaacgag ctgtctgaaa acagaatagg gtgcctcttc aatgtgctct tcactggaga    27420
tgttcaggag gaggctactc ccacctacac agggtgcagt ggagggtctg ggccccaggg    27480
aggcagcagg aagagtggaa agagcggagg ctctactgtt ggacagacct gggttaccag    27540
ccgtgtgact agccttccct ggcctccata tccccctcag taatgaagga atgtgtcatc    27600
cccaaatcca gggacagtta caagcagtca gtgaacagaa agtgtctggt acaggttcta    27660
agtgcttatt attctaagtc acttcactta cctgagttct cagttttcct atctataaga    27720
taagcaggtt ggataaaatg ttctccaata tactcctggt cctgagatga tgtgattgtg    27780
ggcagccctt taatcatggt gaagatgttc atcataagca cactgaaact acaaaatagg    27840
aatataaata ttttctccat taaattatgc tggatcctag aagcaaaaac tggaactgtg    27900
aaaccctact tcacagaaaa cttaaaattc ccaagcagat gaatgcttct cggaaggaca    27960
ctgacagtta cctacctgga aagaatctag atggaggtgg catgggcact aagcggtgag    28020
attaaaccca gttagggcag ccccaccagc cttggaaccc acacatctgg agattgttga    28080
tgcagagaga aaggttccta ctggtgagac ctgaaaggga tatgtggcag gtgggaggaa    28140
gaagttctgt ctggaaacca acccttgttc ctccgttatt gattgactcc tggtaccaac    28200
atgagcccta ggtcttatag aggccataag tccctatgcc ttatagtgcc catggatgag    28260
atgaggccac acatgccccc agtgggttaa catgtctagc gtgggtaagg ctcttggagc    28320
```

```
actatgatac acaggaaatg cccagtaact cttagttggt tgatatctg ttcccattgc    28380 tcacttaagc tcagtgcccc tttactgatc cttttattct gcctccctct gcacatgtgc    28440
attgagactc ctatctgaga cacacactgt gttgggtgcc cagggatgca gcatagatgt    28500
tgctgccttc cacagaagcg ctcatggtct gctagagaat atatcccatg ggagagaaaa    28560
acagactcgg gagaatatag caggggccct tgtcctggac tttggcagtt aggaaaggga    28620
gggaagagac atggaggctg ggacccaaag gctaaatagg aatttgctgg gccaaagggg    28680 aggggggaatg aaaagagtgt ttctggcaga ggaaatggca aggataaagg cctggaggcg    28740
caagagaata tgtgtttgag gatctgaaag ttgagtgcag tgggtccagt gttctctacc    28800
ctggctgcca ttagaattac ctgggaaact tttagaaaat tccagtgtct gggccctccc    28860
taaaacaata aatcattctt gggtggtggg gtctgggcat caggattgtt taaaaccctc    28920
cccaggtact gtcatgtgca gctggggtta agctgtgctg gggtctgagt atggatctgt    28980
tagggcaagt ggcggtgatg gagttgaggc tgcagaattc aggccaaata gagaggtttt    29040
catcaggata ttaaagagtt tagatttcaa tttggtggga atggatggga tcttatttgc    29100
attttatgaa gagctccctg gttgcaatat cagaatggat tggagaggag caagatggaa    29160
gcctacagtg atttgggaga agtggtgagg gacttgagac acaggaagta gccccattca    29220
ctaatagttg agtatgtaga tttgctagga cctggaaatg gtttggctgg tggggagtgg    29280
gaagaaaggc ccaaagtgtg aaatgaagat ggagagcaca ttgcctagcc cagagtgatt    29340
gccatttgct ctgtcccagt tgaggtccaa ggggttggcc agagatcatg gagtctgtgg    29400
ctccatgggg agaagaacct ctcagcatgc ctccttgtct tatcctgggt tagtcagatt    29460
cattttgtta gattacattt tttttccagt ggaactctgc ttaagtcctg accagtatgt    29520
tttcagaagg atcagagggc ctgcccttgt ccattggtgc atgacaccag cttggtgggt    29580
tccttgctgc tccctgtttt catagggtta tcagaatacc ttctctccct gccaccagca    29640
ggtcacactg gctcctgact ttttggccca tggaaccacc atctttctgc ttcttagatt    29700
gtgccttgta ctccactgat catggccagt acatcagaag ccctggtttg cagtgaatgc    29760
atttgatatg gaaatcagga accctgggga taccactcat catatttggt tgctgtgttt    29820
ttcctccaat cttcaccat aacaacaatc aactcaaaag atttctataa ccacttgtgt    29880
gggggtttct ccccacacac taaacaagca gtcagttcca gagtggacag cagctggtct    29940
cctccaattt aattccaaca ctgtctactt ggagatagca ttagatccca caggttgagg    30000
gtgcagtccc ctagactgcc cccagtctcc tgcttcagac accagtcaca agtccaggac    30060
tctagaagtt ctgaccagtt tcaagttggg gttcccacaa cccccactt tattttttgat    30120 taatttgctg gagtggctca tagaactcag ggaaacactt agttttctgg acttattaca    30180
aagatttaaa aagataccaa taaatagcca aataaagaga tatacagggc tagatctgga    30240
agggtctgga gcgcaggagc ttctgtcccc atctacttgg ctcccagcag atggatgagt    30300
tcttattcat tttcttgtca gcttcgacat gttcagctct ctggaagccc gcaaactctt    30360
gtcttcttgg gccttttatg gagacgtcgt taggcaggca tgattgaaac atggacaact    30420
gtgtcgaaat atgattggac ataaaggggg ctaaactcag tgaggcctgt tgttcagat    30480 tcttcttggc ctctctgtgg ccattctttc ctccaggata tggggcagga ccctatgga    30540 atgagggtct tatgacccac aatcaaatta gagtcctgcc ttgggcaagt gaaggaaag    30600 caggagaagg taagagaaat tctgttgcct aagaccttct gaggcctaaa gcaccccaac    30660
attataacag aagacgataa caggactatg ggagttatga gctgggaacc ttggacaaaa    30720
```

```
atatatacat attaaataaa tattaagtgt atatatatac ttacgtatat taagtgtatg    30780
tgtgtgtgtg tatatatata ttttttaat ttactggttg gttttgggaa gcagaaatta    30840
ccataactac tcttaaaaat cttttaagtc tctttgaagt tagaaaagtc actgtacctt    30900
tttgttcca ttggccctgt acttcttatt atacccagc aggaggagca taatgtgttg     30960
ttatatcatt ctggtgataa gattcataag tgggttcagc tggtgacagc ctgattccct    31020
cattgtaaac ttatccatca acatgtagct taatcgtttc accttttgtg atgaccatta    31080
cctgaatcag ttatttcatt agattgcaag attatgcttt tctgatttta tcatttcttc    31140
tgtattgact gtaattcttt ggtatagaag aactttccct tgttaatagc tatttggttg    31200
tcctgaagta cagttcttac tagaaagtaa gaccaaatgc tgaattatat ccctctagct    31260
atcaattttc gaaggaatga atggtgtcct agtaatttcc agtggtgttt aattacgttt    31320
tcccttctct ttctccttct cttattccct ccctctccat ctcctccctc ctcactttca    31380
gtttttgct ctttcagtat tttgtcatag ctgttaacag agcaacatat tttaatcaat     31440
tgtagtcatt tttcttttg gtgctcaaat tatcccgtct tagtcccatg gaagcaagcc     31500
cttggagcta gggccctcta ccttttgatg gatttccatt tgtcttgata atttccttgt    31560
ttctgacaag acaagatgtt gcaggcacat tttatacttt cccagcccaa accctggaat    31620
aggccttttc tccgaggagc tctagttcat tttagtggga aatggtattt agagactata    31680
atctgggatc tgggagtcct cattgctact gagtagtcat tacttttagg cttttccagt    31740
ggtcagagct aggaaatatg tatatttaaa aatggacagt tgaatggttg ttgccaggag    31800
ctgggaggaa gggaagtga gaaattgttt aatgggcaca gagtttcagt ttggggaaga    31860
tgaaaaagtt ctagagatag ctggtggtga tggttgcgca acaatgtaaa tgccactgag    31920
ctctcattta aaaatggtta aaatggtaaa ttttatatat attttaccac aataaaaaaa    31980
agtcttcttc tgggagcacc cccccaagac aaaaatatga aaattttaca ctgatacttc    32040
catttcaaga taatttttaag attataagga ttttgcttaa ttcttgaatt ttatacctgt   32100
aaaccttta tacttcaaat ttcgggcaga attgcttcta taacaatgat aattatacct    32160
catactagct tctttcttag tactgctcca tttggggacc tgtatatcta tacttcttat    32220
tctgagtctc tccactatat atatatatat atatatatat tttttttttt tttttttttt    32280
aatacagact ttgctaccag gacttgctgg cccctctggg gagatggtta aatccacaac    32340
aagtctgacc tcgtcttcta cttctggaag tagtgataag gtctatgccc accagatgga    32400
tcgtacagat tcccgggaac agaagcttga tgcattctg cagcctctga gcaaacccct     32460
gtccagtcag ccccaggcca ttgtcacaga ggataagaca gatatttcta gtggcagggc    32520
taggcagcaa gatgaggaga tgcttgaact cccagcccct gctgaagtgg ctgccaaaaa    32580
tcagagcttg gaggggata caacaaaggg gacttcagaa atgtcagaga agagaggacc    32640
tacttccagc aaccccaggt atggcctttt gggaaaagta cagcctacct cctttattct    32700
gtaataaaac tgccttctaa ctttggcttt tcatgaatca cttgcatctt ctctctgcct    32760
gacttgccct ctggaatggt gctggaatgg tcctgtggcc ttgtccactg tctgcctttg    32820
accataactt gaaagtcacc caccatagtg tcctttgaaa taacttaaat gtccacagtt    32880
ccaagcatga gttaaaaaca cttcagaatg tagagtagtt gttcaattga ataaacacac    32940
acaccagaaa aaaagcaag tttatctttt atttttagta aagaatttg atagagcctc      33000
aacaccagaa atggctagag agagaagcct aacatatctg gaggattatt tttcatccta    33060
```

```
cttaaagctg ctttcacttt tttcaggaaa aaacacacgt tctgaatcta atttataaaa    33120
ctccctggcc gggtgctgtg gctcacacct ataatcccag cactttggga ggctgaggca    33180
ggtggatcac ctgaaatcaa gagttcaaga ccagcctgac caacatggtg aaaccccatc    33240
tctactaaaa atacaaaatt agccagacgt ggtggcgcat gcctgtaatc cccgctactc    33300
gggaggctga gacaggagaa tgacttgaac ccgggaggcg gaggttgcag tgagccgaga    33360
tcgcgccatt gcactccagc ctgggcaaca agagcgaaac tccgtctcaa aacaaacgaa    33420
caaacaaaaa ccccaaaaat ccctgaagta cgtgagctag tggtgaaaga aagctggaga    33480
aaaggagcag gaataataat aataataata ataataataa agattgtcat ttaattttga    33540
gtacttccag tgtacacttt gcaggtactc taagacatta cctcactgaa atctctaagg    33600
tagatattct ttatttaaag tgtacttgta tgaaacctgg agctcaaggt gaaggaattt    33660
gcccaaggct gcacttgcac tatcgtggca ctaattagcc gtgtgaactg ggacacgtta    33720
cttcagtttg ctcatttctg agtcagccta gcaagatgac ttctaagaat tttttccagc    33780
cgggtacatt ggcctgtaat cccagcactt cgagaggcca aggtggaagg gtcacttgag    33840
tctaggagtt acacacaaca cacacacaca cacacacaca cacactagcc aggcatggtg    33900
gcaaatgcct gtagtctcag ctactccgga ggctcaggtg gaaggatcac ttgagcccag    33960
gaggttgggg ctgcagtgag ccatgatcac gccactgcac tccagcctgg ctgacagagt    34020
gagatcctct gtctcaaaaa aagaaaaaaa aaaagatttt tttccaggga ataataaagg    34080
aagctaatat ttatggagca tctacggtgt gccaaatact ttgcatacgt tatctcattt    34140
aatgctctta tccctgcagg gaaagtatta acatttgttt atcacttgca gaactaagtg    34200
atatttacca cagagtagac aaatattttc aagcccaaaa tcaagtggta tcacttttct    34260
gctgagaatg tttcagtggt ttcctttgct cttgggataa aacttaaatc cctcacccta    34320
cccttgctcc aaccctccac tttccttctc ccatgtggtg atttggccat acagctcttg    34380
tggctgatct gaactgactg agcttttttac ccttttgctc ttgctgttct tacagcctgg    34440
gaaccccctg gttacctctt ggcttggtgt ggtggcttac atctgtaatc ccagcactct    34500
gggaggccaa ggcggacgga tcacctgagg ttgggagtat gagaccagca agtcacctct    34560
tgccagtggc ctttgtccat tgagtctgaa gttctttctc ctctcatttc cccatcattc    34620
tattatgcta ccttgttttta ttttcttcat tgtgtttatt gatacttaaa atgatctctt    34680
ttctgttgct gtttgactct cccactagaa agtaagcatt gtagatcggg cactgtggct    34740
cacacctgta atcccagcac tttgtggggc agaggcgggt ggatcacctg aggtcaggag    34800
ttcgagacca gcctggccaa cacggtgaaa ccccatctct actaaaaata caaaaaatag    34860
ctgggtatgg tggctcgtac ctgtaatccc agctactcag gaggctgaga catgagactc    34920
acttgaacct gggaggcaga ggctgcagtg agctgagatc acaccacagc actccagcct    34980
ggaagacata gtgagactct ctctcaaaaa aaaaaaaaa aaaaaaggaa gtaagcattg    35040
tgagggcagg taccttctct gttttgttca ttgctggatg tagttagtat acagcagtat    35100
ctgatggatg gatagatgga ggaatgaatg aatgagactt cacaaattca gctcacttgc    35160
tcaaggccct gcagctctac gggatgaagc tatactccag agtcctgcta cattggctgt    35220
gtggccagct gctgggatct gagggttgtc agataagcag tctaccagag aacagactga    35280
tcttgttggc cttctgccag cacaggggtt cattcacagc tctgtagaac cagcacagag    35340
aagttgcttc ctcctccaaa atgcaaccca caaaatttgg ctaagtttaa aaacaagaat    35400
aataatgatc tgcacttcct tttcttcatt gcagaaagag acatcgggaa gattctgatg    35460
```

```
tggaaatggt ggaagatgat tcccgaaagg aaatgactgc agcttgtacc ccccggagaa   35520
ggatcattaa cctcactagt gttttgagtc tccaggaaga aattaatgag cagggacatg   35580
agggtacgta aacgctgtgg cctgcctggg atgcataggg cctcaactgc caaggttttg   35640
gaaatggaga aagcagtcat gttgtcagag tggccactac agttttgctg ggcaagctcc   35700
tcttccttta ctaacccaca atagcatcag cttaaagaca attttttgatt gggagaaaag   35760 ggagaaaaat aatctctgtt tattttaatt agcattaatt ggtattcttg ttaaaccata   35820
ggagtcagag taaatcagcc atttcaccaa ttttcagttt gtttctgtct tagctaacag   35880
cagtgtaatg gtcagcaaaa ttcttatctt gtgtactgaa tggcatgtcc tgttgctgaa   35940
agtgcacagg cttgggaggt agccatgagc tcaaatcctg cactaccac ctctcttgtg    36000 tgaccttaga ctcctgacct ttctatgcct cagttctttc ttacctataa aatgaaatta   36060 attttacccct taaagatcat cgtgctgatt agagataaaa tataaataat aacacttgtt  36120
acagagcaag gagttgacac ttttatattc tgaagacaaa gtggtaaatc attatcatct   36180
atgtcagaaa tagcttttga gaatacctga gtatagaact atcttgatcc ctgttacttc   36240
aaaactaaaa taatggtttt aggaattaaa aggtgaggct agtcacctcc aagggatgaa   36300
ctgactcagg gattgaggta tataacagtg aactggtcca acaacagtc ctgacccac     36360 tttatgagtg agactatgag taatggtcta agtgtagaca tcattgtcca gggctccagt   36420
aggcagctct gtacttgaga atttagcagt gaccctccta tttttcatct attatacctt   36480
tttttttttt tttttttgac acagggtctc actttgtcac ccagctggag tgtggtggtg    36540
caatcatggc ccactgcagc ctcaacctcc ctgggcttag gtgatcctcc cacctcagct   36600
tcctgagtag ctgtaattac aggcatgtgc catcatgccc agctaatttt tcttttctta   36660 gaggtgggggt tttgccatgt tcccaggct ggtcttgaac tcctaggctc tcacctctgt    36720
cttccaaagt gctgggatta caggtgtgag ccaccacacc tggcctatta cacatttctt   36780
aattaaagta gtcaaatttg aaaactgtta caaagtgtat cttaaaatac gacgatctgg   36840
tttaattttt aaaagatatg agtagccaag gagcaattct gtgcctttcc cactagtccc   36900 taaccttta aagcagctgc ttcttggctg ggctcagtgg ttcaccctg taatcccagc     36960 actttgggag gccaaggcgg gtggatcatg agtcgagatc atcctggcta acacagtgaa   37020
accctgtctc tactaaaaat agaaaaaaat agctgggcgg ggtggcggat gcctatagtc   37080
ccagctactc gggaggctga ggcaggagaa tggcatgaac acgggaggca gaggttgcag   37140
tgagtcgaga ttgtggcact gcactccagc ctgggcgaca gagcgagact ccatctcaaa   37200
aggaaaaaaa aaaaaaaaac ccatctgctt ttgattcagt ggcttcttta attttgtcgg   37260
tctcagtcac catttgtcta agcaaattca ggcaggcttc accttgcctt tctacatttg   37320 ttccctttc ttagcatttt gggcctttgt ttacacgtgg gaaaagaccc acaggtcgtc    37380 tctcccttttg gcaggatac aggcttcctg tgactgaggt tttgctagct gtagaagtgg   37440
ctgccaattg gcttctggtt tttatttcca tgatttgctc cagtggctct tcccttccat   37500
cattgttagc tttcaagcta ggaactttta aaatgctttt aaataaaagt gagctgttac   37560
ttgatgcatt tagcagtctt cctcacagtg gttttgatag acagactccc tcagtttgga   37620
atttatgagt tttctttaag ggtttgtctc cctcatgtat agcaggctgt tgaaagttac   37680
aatgtcaata actttctgaa tagtatcaaa ctgtttcag tgcagtgtat taacaaaact    37740
aacctgcctc aagtttggtc agctttggag tcttactgag gctaaaatga taaatctaaa   37800
```

```
tgatttaaaa ttgtgtattc ctacacagta tctcacttaa ttatgtaata gtcttgtgag     37860
tgaggcagag cagatgccgt tttctctatt ttaaagatga ggaaaatgga atggaaaatg     37920
gaaaggacag actaattgca acatcctcgc aatcaaaaac aggcccaggt tcatgccttg     37980
ttggcagtgg gttgctactg gctgtggcct tcatgcagga aggctagatg cataaccagg     38040
tcaacagccc gtgcaggaca agcacgccat gtaattctga ttccatcgac tgaggctggt     38100
gttttcaaac gtgctggtgt agggtcttac agacagagtc atctgtgcta tggggaatgg     38160
aatgtgctct tgctttggag ccagaactcc tctgaagctc ccaccaccta caccattcag     38220
aggccagaca gaaatttgtt caccattttg ggcatgattt tcgtgctttt gtaaaatgtg     38280
cttcactgca gcccttactg ggctgtggtg atgaacactt aagatactgt gtgtgtgctt     38340
tataatctgt aaggcactgt tcaaggggag ggacctctgc catgagcccc tacccactgg     38400
tatctggttg acatccaaag ccccagcctg ggagaagctg attctctagt tgaatgctgt     38460
atagggattt gactgaggct cagatttggt gaggaagacc actaacctta acagaccaac     38520
aggctggcta ctccctgatg aagttcccca ggccatgaaa aagtaagag atacattcct     38580 tgtaacagct ttcttagttg cacctgtatg attatttgat cagtgtgttg tctgtgcagg     38640
gatcatgtct gtggagctca ccacctcgtc ctcggtgctg agcagagtgc ctggcatgtg     38700
tactcagtag atatttgcta agggagcgag tcagtgattg agaggagcag cctgggaggt     38760
aaagccctag aatcttattt ttaaagggat atcaaagttg aacattcagt tagacagttc     38820
tcttgagtcc agggatttac ccatccatgg tggacacact ttcagttaaa aagtaaggtt     38880
aattttgaca ggttgcagta tccaggcaag cattctatgg aataaggctc atctcaggga     38940
ttagtaatga ctgaattaac ttactgctag tcccataatt ttgacgttaa ttaatggggt     39000
taagaaatgt cataagctat ttggtaccat ttaaagtgaa aatacccta acgttttttg     39060 cctccagata tccacactta atttcatttt cttgctcttt ggtgaacagt cctgggtctg     39120
aatgtatata tccatggttt gtcactaggt gacaggtttt tttggaacaa gaatcagtt     39180 cagtgaacat ttgtcaagta tcttctctgt aaaaagtgta atgtgccaag ctcagaagta     39240
ggaagtgaaa tggataaact atgacccctg ccttaaagaa caccatggtg ttgtatggga     39300
attgtttagg tagaatgaaa gaaatcctct aatagagata tgaggccagt tcagcagaaa     39360
gccagggtga gatctcctga gagggatgga agggtgtctt gatcatctct ggtagcagca     39420
aaggcactgg catacagtgg ccactggaag acaaccagca ggggatgggg gcgtttaccc     39480
ttgcaagtga gcattaggaa ctagaggact gattgcccct tcttcagctt tggtttccct     39540
tgctgcagaa aaagatgctg agactcatgg cctcggttat gaactcagat atgtggtttg     39600
gctttgaagc acagatggat tttgtccgat tttggcaggg aaatgcctac agacagcact     39660
atgggcatat ttaggttagg gacgaaatgc aagttgatta agtcctgata agaggctgtg     39720
aagaggtcca agaagcctca caatgcccaa tgaagaaaag ccctgtgctt ggtgctgccg     39780
cctcccttcc ccgtcctgct ggcagggctg cgcttcagta gctctggatg cgtcagagca     39840
gtccatgaac attctgtgtg gaaaatctct gactgtttta gtggattaca ctgctctccc     39900
tttcctccag tgcctcgtta ttcagtatta tttgatgttc tccagctttt aaaataatca     39960
ttttccgcct acgcagaaca tcctgtagag acgttgaggt tccagtggga acagagagga     40020
atacttattc taaaaatgaa gaaaataaac cttttttat ggagtgggtg atagtattgc     40080
agaacttcta taatagtatg agaattcact tgtggtgcca aagcttaaaa aaaaagtata     40140
gtaaaaacat aatgtatagg cttattgctg tgctatgacc catgccccgt tttctccaac     40200
```

```
ctctcttgtc ctcactcttc cttttttgctg gtgatatttt tacttatttc atgaaaaaaa    40260
agataacata tacacacaca tagatatatg cacaagtata tgtatatatg tgtgcataac    40320
acacataaac atatacattg gtaaatttaa aaacatatttt atgaaatata tgtagcatct    40380
acagaaaaac atgaacactt gtgagaatag catctgccta aaaaatagga catcaccatc    40440
acctttgagg ctcttatgtg ctgctcccct gtgccattcc cttcccttct tccttagagg    40500
tgattactat tctaaatttt gggattatta tttccttttt ttattatagt gttttaatta    40560
cagttttatt acctgtattt gtattcctaa aaatttgttt acttttgcaa gctttagatt    40620
ttataaaagt agaattacac tgtaagttta attttttctgt aatttatata tagctacaca    40680
tatattccta agattcatcc atcttgttac atatagctct ggtttaccttt ttctgtataa    40740
tatagattct gcttcgtgaa tttacagttc attcattctt ctgttaaagg acagttggag    40800
gactcatatg gcctcagtct ctgtgtcccc acatgccacc ctgcttccca gcctcatatg    40860
agttgattgg tggcctggca tactggatga gaagctctag gtcatatatt taagagagtt    40920
attgctgggt cataaaatga cagattgttt tccagagggg tcatattgat ttaaattatc    40980
accaacaatt atattgtcag attttttacca gtttggtgat tgtgaaacag tgtctgatgg    41040
tagtttttat ttgcattttc ttggttgaaa taaagttgtg tatttcagcc aggtgcgttg    41100
gctcatgcct ataatcccag cactttagga ggccaaggtg ggcagatcac ttgaggccag    41160
gagttcaaga ccagcccagc caacgtggca aaaccccatc tctactaaaa atacaaaaat    41220
tagatgggta tggtgtcaca tgcctgtaat cccagctact caggaggctg aggcacaaga    41280
cttacttgaa cccgggagat agatgttgca gtgagccgag attgtaccac tgcactccag    41340
cctgggcaac agagcaataa ctaaataaat aagtaatcaa ttaataaata agtatatttc    41400
ctcagctgtt aagtacctgt tcaagttttt tacccaatat ttgatgggct ctttttttgt    41460
cttttctaat taatttttgg agttttttgat atattctaga tagtaatgag ttacatgaaa    41520
atatccctag tttagggatc ctctagtaac ttttttaaaat gaatacttgt tttaggaaca    41580
gaaattctta gatttaatgt aggcagattt tatcaattgt tctttacaga ttggcttttgt    41640
agcttaagaa atccttccta actttgcaat aattaaagat atgctcttag attgtttcct    41700
aaaagactga tacttaagcc tctagcccac ctggaattga ttttcacaga tactacatttt   41760
tttactagtt atagattggc cccttcgtag agcaagtccg atagctgcca tttttatggc    41820
agcatgtgct cacttagtgt ctctgtcaaa ttttggtaat tctcacaata tttccaactt    41880
tttcattatt actatatctg ttatggtgat ctgtgatcac tgatctttgg cattactatt    41940
gtaattgttt ggggcaccat taagctcact gtcttatgtg ggcataaacc atgcccacat    42000
aagacagtga gcttaattaa taaatgtgtg tgctcagacc cctccactga ctgggtgttc    42060
acatgtcttc cttactctcc tcaggcctcc ttattccttg agacgcaata atatggaaac    42120
taggcaaatt aataacccca cagcgtccac aagtgtttaa gtgaaaggaa gaggctgggc    42180
gcaatggctc acatttgagc tcacaaatga gcccatgctc atttgccatt ccaaaaatcc    42240
cagggccctt aagaattatg ctaactctac tctgcctctg ctctataaat ggaacaacaa    42300
agcctagatg acagcacatc ttttttagaac atgatttact gaatattta agcccattgt    42360
ggagacctac tgctcagaaa aaagattcc tttcaaaagc ctgtaatccc agcactttgg    42420
gaggccaatg caggtcgatc acctgaggtc aagagttcga gaccagcctg gccaacatgg    42480
tgaaacacgt ctttattaaa aatacaaaaa ttagccaggc ctggtggtag atgcctgtag    42540
```

```
tcctggctat tcaggaggct gaggcatgag aatcacctga acccaggagg tggaggttgc    42600
agtgagccga tatcatgcca ttgcactcca gcctgggcac cagagtgaga ctacgtctca    42660
aaaacaaaac aaaaaaaaaa aactgaaagg aagagcttaa tgagaaaggc atattaaaag    42720
ccagtatagg ttgaaagcta ggcctcttgt gcaagttagc caagttatac atgaatggta    42780
aagcaaaaca gctttattgc tgtaataaag aaagttttag tggtctggat agaagatcaa    42840
atcagtcaca gcattccctt aagccaaagc ctaatccagg gtaaagccct aacttgcttc    42900
aattctttga agactgagag gggtgaggaa gctacagaag aaaacttgga agccagcaga    42960
gattgatgag gtttaaggga agaagccaca agtgctgatg tagaagctgt agcaagttat    43020
ccaaaagatc taattgatga aggtggctta cactaaacaa cagattttca atgtagacaa    43080
aacaatcttc tattagaagg tgtcatctat gacttacata gttaaagagg aaaagtcact    43140
gcctggcttc aaagcttcaa aagacaggtt gactctaata ggtactaatg catctggtga    43200
ctttaagttg aagccagtgc tcatttgcta ttccaaaaat cccagggccc ttaagaatta    43260
tgctaactct actctgcctg tgctctataa atggaacaac aaagcctaga tgacagcatc    43320
tttttagaac atgatttact gaatatttta agcccattgt tgagacctac tgttcagaaa    43380
aaaagattcc tttcaaaata ttactgctca ttaacaatgt acctggccac cctagatctg    43440
taatggagat atataaggac atgaacacta acacagcatc cattctgcaa cccatggatc    43500
aaggagtgat actgactttc aagtcttatt taagaaatac atttcatagg gctctagctg    43560
ccatagatag tgattcttct gatggatctg agccaagtaa attgaaaacc tctggaaaga    43620
attcatcatt ttagatgtcc tgagaaacat tcgagattcc tgggaagaag tcaaaatatc    43680
aacattaaca ggagtttgga agaaattgca tccagccctc atggataact ttgaggggtt    43740
caagacttca gtggaggaag tagctgcaga tgtggtggaa atcacaagaa aattagaatt    43800
agaagtggag cctgaggata tgactgaatt gctgcaatcc catgataaaa tttgaacaga    43860
tgaggagttg cttcttatgg atgagcatag aaagtagttt cttgagaaag aacttaattc    43920
tggtgaagat gctgttaata ttgttgaaat ggcaacaaag gatttagaat attatataaa    43980
cttggtaaag cagcagcagg gtttgagtgg attgacacta gttttggaag aatttctact    44040
gtgagtaaaa tgctatcaaa caacatgaca agctacagag aaatctttca tgaaaggaaa    44100
aatcaattga tgcagcaaac ttcactgttg tcttatttca agaaattgca acagcttcct    44160
cagccttcag caatcaccac cctgatcagt caacagccat catcagggct agatcctcca    44220
ccagcaaaaa gataacaatt cgccgacagc tcagatgact gttaccattt tttagcaaaa    44280 accttttttaa ttttatttat ttatttattg gagacagaga ttcactctgt cgcccaggct    44340
ggagtgcagt ggcacaatct cagctcactg caaccaccac ctcccaggtt caagtgactc    44400
ttgtgcctca gcctcccaag tagctgggat tataagcatg tgccaccacg cctggccaat    44460
ttttgtattt ttagtagagg caggatttta ctatgttggc caggcttgtc tcgaactcat    44520
gatctctggt gatctgccca cctcgggttc ccaaagtgct ggtattattg gcatgagcca    44580
ctgcgcccgg ccagcaaaaa agtgttttta aattaagcta cctacgttga ttttagacat    44640
aatgctattt gcacacttaa tagattacag tgtggtgtaa acataagttt tatatgcact    44700
gaaaaacaaa aaatttcaca tgacttgctt tattgtgata ttgactttat tcctgtagtc    44760
tggaactgaa cctgcaatat ctcagaggta tgcctgtatc tacttgttct gtgatacttg    44820
ttattgtcag tttgtttgga tttaccacat attatttgat cataattctt tcctgtagat    44880
gttttatggt ctgcctaaac ctttagtggg gcctttgatg gcttagtcct ttcaggctta    44940
```

```
agacaataga agtttatttc tcagagttct aaaagctggg aagtccaaga tcaaggcacc    45000
gacagattta gtgtctagtg aaggcccgct tcctcataca tggcaccttc tagctgtatc    45060
cttacatagt ggaagggaat agctagctct ctggagtttc tttcataagg gctaatccca    45120
ctaatcccaa ttatgaggga agacctaatc acctcccaaa ggccccacct cctaatagta    45180
tcaccttggg ggttaggatt taacatatga attttgtggg gacacagaca ttcaaacaat    45240
agccatggca aacttttttg ctttgtctaa ttcactctta ttttgaaaag tatttgtgtt    45300
gggtttaaaa ctccagattg gtaattattt tttcttagtg cattgaaggt aatagtgtat    45360 catttttctga tttctactct tgctcttgaa aattcagcta tcaatcttaa aatttattac    45420
ctgttgaaaa tccagctacc agtcttatat tttatttact tagtgggtaa tctctcttct    45480
gagtaccttt aagatctcct ttcagaaata ccatgtagta accctgtgtg tcacgtgtgg    45540
attttgttgg gcttgctagc tgagacttga cagttttcat cacttctggg atattctcag    45600
gtattttgtc ttcaaagtct tcagatattg tcctcttcct gccctctctc cgactccttc    45660
tggaacatga gttatgtatt tattatctcc catgtgcata agttatcttt acatattttc    45720
aatttcttta tctttctgtg ctacattctg gataattttg ttgatctacc ttccagttaa    45780
ttagcttgtt aactttgtca aatctctttt taagtctatc ttgattttc ttttcaatta    45840 ttgtatttttt catttttaaa aactttatgt gctcttttgg aaatcttgat cccaggagat    45900
agtggatagt gtcctgctgc ttactcatgg ttttaatagt tcttgagcat gctgaacata    45960
cttattttat gttatttgct aatctttcca attcctgaaa cctttacaga tctcattctg    46020
tggattcttc tggattctaa ttcatggggc attttttttg tttttttgtta attcctcata    46080 ctttatctgt ggggaattac ttgaagcctg ggttgacaat gaaattctgc agagagaatt    46140
tgcatttgat tctactggag gaacagtcag ccccgatatc agtttaaatt aaaatctctg    46200
cttaaggttt tcaggcaacc tgcttagcat gaatcctggc tggaaaagca tgtgaggacc    46260
agtttatgat tacacattca cagggtgtca tgttttcttc caacaccaat gctagaggtg    46320
gcagttttgc ttactgccct tggagggaca ggggagtggg catggcata gtagtatggt    46380 tttcctttc actggggtg cagcccttgg agtctcagct taatgtgttg gggaagtggt    46440
ctcctattag actctccatt tcaaaccatt ccatgatttt gtcctccttt tgccaccttc    46500
cgagcctgta aaaactaatg tttgtgattc ctgaggtttc tctaatgtct tttaataaag    46560
ttgacctcag agatctcgtt acctctctga gttcctgctt tgtcttagat tttgatcctt    46620
gagtgttctt taatcttttta gcaattcctt gttgcatgtt aaaagattag ttatatttta    46680
ttcctcattt gtgttcgttt tcaccaggag gctcaattca ggcttctttg cttacttggt    46740
gtctctagtt ctggtgcctg gtgctttggt caatgaagtg gggttggtag gattctatta    46800
cttacctgtt ttttggtttt attttttgtt ttgcagttct ccgggagatg ttgcataacc    46860
actccttcgt gggctgtgtg aatcctcagt gggccttggc acagcatcaa accaagttat    46920
accttctcaa caccaccaag cttaggtaaa tcagctgagt gtgtgaacaa gcagagctac    46980
tacaacaatg gtccagggag cacaggcaca aaagctaagg agagcagcat gaggtagttg    47040
ggagggcaca ggctttggag tcagacacat gtggtttcaa atccaagttc gaccatttcc    47100
catttatttg actgtagaca agttacattc ctaaactatg tctcagattt ctcatctgta    47160
agttgtggta ttactagtta acatgcaggg gttttgtttg tttgtttgtt tgtttgtttg    47220
tgagggtaag aaataaccca agaagcctag tccttggtag ttgctcagtg ccctataaat    47280
```

```
gttgtgaacc aggtggtgag ggtttggtgc tgctagagaa ttctggtatc tgctctgtgc   47340
aacagagtac tgtaggtgat gcaagagaaa gaagacctga tgccttcttt cctcccagct   47400
ttgagaatgg agcaaaggcc taccccagcc accaagtgag ccagtgggct tgatcagcac   47460
aggaaaggtg accccggcag tttcatttga ctattgcatg gctggcaaca tttctattga   47520
ttgtttccag ggaccttggc ggatgagctc ctgttgagtc tagcatctct gttaaatctg   47580
ttctcaaata ggtaatgcat atgggaggat gctgccacct tgcatctact agacatcacc   47640
tatctactgt gagactctcc ctctaagccc tgctgtggcc tcagagtgct tattggccct   47700
gtgagtgggg cagccactat acattgcatg gagttggtac atgagataga aacctattcg   47760
ccatcccttg aaactgcccc agtccagaag cttcctgtta gcacatgtac ctccttgtat   47820
gtattcagaa ctcattccat ttaggcttgg aaacccgttt ggtgcaactc tgttcaagtt   47880
ccattgtctg ctttgagaat gcttgggctt gtatagtgag ctgtcacttt ttaatttgtt   47940
aggaattcta ctcgccttgc ttttctttt ccagcatgtt taagggaatg acctccaagg   48000
ccccaaatca cagttgtatt catgttcttt catttcacag atacaatcca ggccagtccc   48060
agatttgcag ctgttaataa atgtgaatgg ttttccagta aggggtaga aaaacatagg   48120 gagagaaccg ggttcagagt tcaatatctg gattcaagtc cttcctttag cactttacta   48180
actgatgtag aataagtcag ctactcaata ggtgcctcag tttccccacc aaaatgcaga   48240
catagaaggt gctttgtctg ctttgatgag aagtctttaa gcaagtctat ggggttcaat   48300
gtgttttaag aactataaag taccatataa atgtggcctt tattcccatt gtgttcttgg   48360
aagtaattca atatagtgtg tacttcatag ctgcttttgg actattgcca gccagtgtat   48420
catcctaaac tacatgtcag catagtataa tcctgcctta ggtctacttt tgattattta   48480
ggaagactcc ctgcccttcc tatacatttc acataatttt taataagttg taaaaaagtg   48540
atttatagga ttctttgtaa gtgggggaag ttaagcagac aaaaagtttt taaatcttac   48600
tgcagagtgt caggaacctt ttatagcacc agacaggtag ggacagaaca tgagtggcag   48660
caagccagac ttggtcttag tgctctaacc tgtctgttag aggctggcca gtcagacccc   48720
tggttgaaga cgttgggaat cccagctctt tggaggggta agagattttg ttagactgtt   48780
aaccagattc cacagccagg cagaactatt tctgtctcat ccatgtttca gggattactt   48840
ctcccatttt gtcccaactg gttgtatctc aagcatgaat tcagcttttc cttaaagtca   48900
cttcattttt attttcagtg aagaactgtt ctaccagata ctcatttatg attttgccaa   48960
ttttggtgtt ctcaggttat cggtaagttt agatcctttt cacttctgaa atttcaactg   49020
atcgtttctg aaaatagtag ctctccacta atatcttatt tgtagtatgt taaattttc   49080 taaaacttct aaggatagtt gctgtattgt atgatttgca tatggaggta tctataagaa   49140
gttttatact ttttagcaaa atagtcattt ggtagccaac ttaaacaaat gtttattaat   49200
atagaagtta ataatatcta ctgatactcg gccgggtgcg gtggctcatg cctgtaatcc   49260
caccactttg ggaggctgag gcgggcagat catttgaggt caggagttca agaccagcct   49320
gaccaatatg atgaaaccct gtctctacta aattacaaat attagcaggg tatggtggtg   49380
ggcgcctgta atcccagcta ctcaggaggc taaggcagga gaatcatttg aacccaggag   49440
gcagaggttg caatgagctg agatcacgcc actgcactcc agcctgggca acagagcaag   49500
attccctcaa aaaataaat atctactgac acttaatact tggaagggga taaaaataaa   49560
cattgtctaa agccgtggtc caaacacaac ccctgccaac aatttagtc catttcttcc   49620 aagactttt tttttctatg ccttttgtga aaactgtcaa aaactttttc aatgctgaat   49680
```

```
tttagttctg agttaaaaat catactacct gtttatatgg tttcatatcc acttttttca   49740
tgtgatatac tctacaaaaa gcctgctgag attttgattg ggattatgtt gaatctagat   49800
caatttaggg tgaaaaactt ttgttagata aatcccttag tatttcacat ttttaaatgc   49860
taaatggcat ttttcaaaaa ttttcttttt tcttttcttt tttgagacag agtcttgctc   49920
tgttgcccag gctggagtgc aatggcaaaa tcttggttca ctgcaacctc cgcctcctgg   49980
gttcaagcga ttctcaaact gcctcagcct cccaagtagc tgggattaca ggcatgtgcc   50040
accatgcccg gctaattttt taaactattt atagtagaga gggggtttca ccatgttggc   50100
caggctggtc ttgaactcct gacctcaggt gatctgccca ccttggcttc ccaaagtgct   50160
gggattacag gtgtgagcca ctgcacctgg cctcaaattt tttttttttt ttttttttaag   50220 agacaggggt ctcactcttg cctaggctgg agtgcagtgg cgtgatcata ggtcactgaa   50280
gctttgaact cctaggctca agtagctagg aatacaagtg tgtaccacta cacctggcta   50340 attttttttaa aaaattttt ttcgtagaaa cgggagtctt gtgttaccaa ggctaatctc   50400
aaactcatgg cctcaagtga tactcttgcc tcagcctccc agagtgctag gattgtaggc   50460
atgagttact tcacccagcc aaaaaacttc aatttcctat tgtttatttg ctagtatata   50520
gaaatacata tagttttgta ccttgatgct gtatcttgca accttgttaa actcacttac   50580
tagttctagt atattttttg tagattctat cagattttct atatatgtat catgtcttct   50640
gagaataaag aaacttttac ttcttgctgt gcaaactgaa caccttttct ttctttcttt   50700 cttttttaa gacggagttt gctcttgtc acccaggctg gagtgcagtg gctggatctc   50760
ggcttactgc aacctccacc tcctgggttc aggcaattct cctgcctcag cctcctgagt   50820
agctgggatt acaggcgctc gccaccacgc ccggctaatt ttttgtatt tttagtagag   50880 atggggtttc accatgtggc cgagctggtc ttgaactcct gacctcaggt aatctgcttg   50940
tctcggcctc ccaaagtgct gggattacag gcgtgaatta ctgcgcccgg ctgcctttta   51000
tttctttctc ttgactgact gcactggcta gagcctccaa tacaatgttg aatagaagtg   51060
gtaagaatgg gccaggcatg gtggctcatg cctctaatcc tagcactttg ggagagtatg   51120
gtgggcaggt tacttgaggc caggagtttg agatcagcct ggcgaacatg gtgaaactct   51180
gtctctatta aaaatacaaa atatagttgg gtgtggcagt tcacgtctgt aatcccagct   51240
acttgggtgg ctgaggcatg agaatcactt gaacccagga ggcggaggtt gcagtgagcc   51300
aagaatgcac cactgcactc cagcctgggc aacacacaca cacacgaaaa acgaagtggt   51360
aaggatggaa atccttctct tcttcctgat ctaaggggga aaggggaaag ttacaaaaca   51420
ttcagtatgc tgttagccat ataggttttt ttgtagatgc ccattatgag gttgaggaag   51480
ttccctctgt tccttatttg ctacagattt tatttaggat tggatgttga attttttttca   51540 aatgcttttt ttgcatctac tgagataatc atatgatttt tctttatag tttgttaata   51600 tagtgaatta cattgatttt cttatgttaa accaatcttt gcattcctgg gatgaactct   51660
gcttggttat aatatataat ccttttattt tattatggga tttgatttgc taaaattttt   51720
attataatta ttttatctgt gctcatgatt gttactagtt tatagttttc ttttagtctt   51780 tggttttgt atcagggtaa tgctggcctc atagaatgag ttggtaagta tcccctcctt   51840
ttccattttc tgaaagagtt ttgtgtagaa ttgatgttaa aattattgct taatgtttgg   51900
cagaactcaa cagtgaagcc atctgggctt ggagattttc ttcatgggaa ggtttttaac   51960
tgcaaattct atttctttaa tagtatagag ctattcaggt tatctgtttc ttcttaggta   52020
```

```
agctttggta ttttgtttct ttgaagaaat ttgtcgcatt taatctaaat ttttaaattt    52080
actgacataa agttatttat aatatttctt attcttttat tatctatgga tctcttggtg    52140
acataacctc tctcattcct aatattggta atttcaggct tttctttta acttggtcag     52200
tctggctaga ggtttatcaa ttttattgat cttctcaaag aactaacttt tggtttcata    52260
gattttccta ttttctattt cattgatatc tgctctgact tttaatcttt cttataccta    52320
ttttggttta atttgtcttc tgtttcacat ttctttttt tttttttttt ttttttttga    52380
gacagagtct tgctctgtcg cccaggctgg agtgcagtac agtggtgcga tcttggctca    52440
ctgtaacctc agccttccag gttcaagcga ttcctgtttc taagcctccc aagtagctga    52500
gattacaggc atgcaccacc agctaatttt tgtatttta gtagagatgg ggtttcactg     52560
tgttggccag gctggtctca aactcctgac ctcaggtgat ccacctgcct tggcctccca    52620
gagtgctggg attacaggtg tgagccactg tggctggcct gtttcacatt tcttaaggta    52680
gaagctgagg tcacggattt gagacccttc ttcttttcta atacaggtgt taagtgctac    52740
aaatatccct taagcactgc ttcaacagca tcccacaaat tttgatagtt tgttttcatt    52800
ttcattcagt tcaaaatacc ttctaatttc ccttttgatt tcgtctttga cctacaggtt    52860
ttttagaact gtgttattta gtttccaatc tcttgaggat ttttaaaaca atatgttatt    52920
gatttctaat ttatttccat ctcagtcaaa gaacatactt gcctttttt atacatttat    52980
tgaaactttt tttatggccc agaatatggt ctgtgttggt aaatgttcca tgtgtacttg    53040
aaaataattt gtattctgat ctcattgagt tgaatgttct aggtatatca agttgatagt    53100
gatgcccaag tctcctgtat ctttactgat tttctgcctg ttctgttatt gagaaagggg    53160
tattgaaact tccaactata attatgattt gtctgttctc tttgcagttc tcttagtttt    53220
tgccttcata tatatataca tatatatgta tatatatata tatttttttt ttttttgagat   53280
ggagtcttgc tctgttgccc aggctggagt gcagtggtgt gatcttggct cactgcaagc    53340
tccgcctccc aggttcacgc cattctcctg cctcagcctc ccgaatagct gggactacag    53400
gcgcccacca ccacgcccag ctaatttttt gtattttag tagagacagg gtttcaccat     53460
gttagcaagg atggtctcga tctgacctcg tgatccgccc agcttagcct cccaaagtgc    53520
tgggattaca ggcatgagcc actgcaccca gcccatatat tttaaagctc tgttattggg    53580
tacataaaca tttaggattg ttatatcctt ttgataatgg actcttctat tatgaaagaa    53640
taatatactg tgggtttata acatatgtaa aagtatgagt aacatattat cagaagggga    53700
gaaatggaag ataacttagg catcttattt ttaagcatag ttttcccttt gtttctgcat    53760
tagatgattt acctgaaatg tcattcaatt taacttactc tccatcctca cccgcccagc    53820
tttggttatg aggcagtaga agaaatgat ctgcctgtgg ttttctagaa atacgaaagt     53880
tgagtcctta aggctacaca gaaagaaagt acctccccag ggcttcaccc ttcccatcct    53940
ttcagcaggc ttttgtctg tcgtatcttc tctgttgaaa tggccattga caagaggagg    54000
aaagggttt tgttgtggat tgttcaggca cttcctttgg ggtatatggg ggatgagtgt    54060
tacatttatg gtttctcacc tgccattctg atagtggatt cttgggaatt caggcttcat    54120
ttggatgctc cgttaaagct tgctccttca tgttcttgct tcttcctagg agccagcacc    54180
gctctttgac cttgccatgc ttgccttaga tagtccagag agtggctgga cagaggaaga    54240
tggtcccaaa gaaggacttg ctgaatacat tgttgagttt ctgaagaaga aggctgagat    54300
gcttgcagac tatttctctt tggaaattga tgaggtgtga cagccattct tatacttctg    54360
ttgtattctt caaataaaat ttccagccgg gtgcggtggc tcatggctgt aatcccagca    54420
```

```
ctttgggagg ctgaggtggg cagataactt ggggtcagga gttcaaaacc agctggccaa    54480
catgatgaaa ccccgtctct actaaaaaaa tagaaaaatt agccaggcgt ggtggcgggt    54540
acctgtaatc caagctgctc aggaggctga ggcagaagaa tcacttaaac ccaagaggta    54600
gaagttgcag tgagccgaga ttgcaccact gcactctagc ctaggcgaca gcgagactgc    54660
gtctcaaaaa aaaaaaaaaa gaacgttcca aggtcaggac taggcctccc ctcagaagca    54720
gcaagtgaca tatgtgacat cctctccact ccctatttgc atttctaggt tatataactg    54780
tactactatc catgcatgcc tactcttgtt cccagggtga aggacccaga catggagagc    54840
cgaatccctg caggccatta taaatgagat tatgccattt gctcccattt cttcttattc    54900
tttcattttt ggggctctcc atcttgatgt gttctttgga tcgtgaacag atccaaagaa    54960
aaggttgttc tgccgtgctg tttgtcagga tgaaaaactc ttttttaagt gtttaggtct    55020
gcccccagtg cccagcccaa tcaagtaacg tggtcaccca gagtggcaga taggagcaca    55080
aggcctggga aagcactgga gaaatgggat ttgtttaaac tatgacagca ttatttcttg    55140
ttcccttgtc cttttttcctg caagcaggaa gggaacctga ttggattacc ccttctgatt    55200
gacaactatg tgcccccttt ggagggactg cctatcttca ttcttcgact agccactgag    55260
gtcagtgatc aagcagatac taagcatttc ggtacatgca tgtgtgctgg agggaaaggg    55320
caaatgacca ccctttgatc tggaatgata aagatgataa gggtgggata gctgaaggcc    55380
tgctctcatc cccactaata ttcattccca gcaatattca gcagtcccat ttacagtttt    55440
aacgcctaaa gtatcacatt tcgtttttta gctttaagta gtctgtgatc tccgtttaga    55500
atgagaatgt ttaaattcgt acctattttg aggtattgaa tttctttgga ccaggtgaat    55560
tgggacgaag aaaaggaatg ttttgaaagc ctcagtaaag aatgcgctat gttctattcc    55620
atccggaagc agtacatatc tgaggagtcg accctctcag gccagcaggt acagtggtga    55680
tgcacactgg caccccagga ctaggacagg acctcataca atctttagga gatgaaactt    55740
gcccatctct aaaatttcgg gatttctttg tacccaacaa ggttcaaaca caacagtcag    55800
cttttattca tgattttttac ttccatctgc tgatgtagaa catacctcca gagtgacctc    55860
agaaattgtc aaatgtgaaa acacaagcca tcacagtgag aaatgggagg ttgagttaga    55920
ttgtctaagg ctggagagtc catatactcc cactgttagc tctgaagtgt gtagccagtc    55980
ttcagattct gggtcagttg cctcagtctc tcttagcttt tgccttactc tttatccgac    56040
cactgccctg ccaggaaaac aaggctctat aactcctctt acaggtcagc ttgacacaaa    56100
aagggtgcct ggattcctaa tgtttcattg tcactttttcc cagtcagatg ataatgcttt    56160
tcaaatcaac atatattttg ggggaggttg gaagggagag ttgaaatatt ctaagaatca    56220
aagagtagcc cactttaatc agagtatgac ccctgattgc tcacagtcat ctcctgagca    56280
gtgtgagcga gtttcagatg aggaggctga aggccagtca ggcatgctcg aggattccaa    56340
gtctgtaggt ggggagggcag agatttagtc ctgttggcca aagcctctag ggaatttctc    56400
actccagtgg agaaggcaac acacttacca aactgtgtgg aaactatctc atttgattag    56460
aaattttacc tcaagaagag gaaggacagt tgagaaagaa catttttctta cacatgagac    56520 agctaaggct tacaagaagg agaggaataa tgaggcaaaa taatcctcat taatattttc    56580
attcctcccc tggggattag aactactttc agacccgatt ttaatggtaa gttaggtact    56640
tcctacagtt gccatccaaa tatcagtcag gatcagacat gatgttagct cctgctacaa    56700
taaaaccatt ttctccctga atgaaaacaa aggttccaca ggagacagtc ccacagagca    56760
```

| | |
|---|---|
| gtggcttctt ttcctcccTT taaaacctca tgttggctgg acacagtggc tcacacctgt | 56820 |
| aatcccagca ttttaggagg ctgaggtggg aagatggctt aagcccagga gttTGAGGCT | 56880 |
| gtagagctat gatcacacca ctgcccttca gcctgggtga cagagcaaga ccttgtctct | 56940 |
| aaataaacaa acaaacaaaa aatcctcttg tgttcaggcc tgtgggatcc cctgagaggc | 57000 |
| tagcccacaa gatccacttc aaaagcccta gataacacca agtctttcca gacccagtgc | 57060 |
| acatcccatc agccaggaca ccagtgtatg ttgggatgca aacagggagg cttatgacat | 57120 |
| ctaatgtgtt ttccagagtg aagtgcctgg ctccattcca aactcctgga agtggactgt | 57180 |
| ggaacacatt gtctataaag ccttgcgctc acacattctg cctcctaaac atttcacaga | 57240 |
| agatggaaat atcctgcagc ttgctaacct gcctgatcta tacaaagtct ttgagaggtg | 57300 |
| ttaaatatgg ttatttatgc actgtgggat gtgttcttct ttctctgtat tccgatacaa | 57360 |
| agtgttgtat caaagtgtga tatacaaagt gtaccaacat aagtgttggt agcacttaag | 57420 |
| acttatactt gccttctgat agtattcctt tatacacagt ggattgatta taaataaata | 57480 |
| gatgtgtctt aacataa | 57497 |

<210> SEQ ID NO 3
<211> LENGTH: 2662
<212> TYPE: RNA
<213> ORGANISM: Homo sapiens

<400> SEQUENCE: 3

| | |
|---|---|
| gaagagaccc agcaacccac agaguugaga auuugacug gcauucaagc uguccaauca | 60 |
| auagcugccg cugaagggug gggcuggaug gcguaagcua cagcugaagg aagaacguga | 120 |
| gcacgaggca cugaggugau uggcugaagg cacuuccguu gagcaucuag acguuuccuu | 180 |
| ggcucuucug gcgccaaaau gucguucgug gcagggguua uucggcggcu ggacgagaca | 240 |
| guggugaacc gcaucgcggc gggggaaguu auccagcggc cagcuaaugc uaucaaagag | 300 |
| augauugaga acuguuuaga ugcaaaaucc acaaguauuc aagugauugu aaagagggga | 360 |
| ggccugaagu ugauucagau ccaagacaau ggcaccggga ucaggaaaga agaucuggau | 420 |
| auuguaugug aaagguucac uacuaguaaa cugcagcccu uugaggauuu agccaguauu | 480 |
| ucuaccuaug gcuuucgagg ugaggcuuug gccagcauaa gccaugugc ucauguuacu | 540 |
| auuacaacga aaacagcuga uggaaagugu gcauacagag caaguuacuc agauggaaaa | 600 |
| cugaaagccc cuccuaaacc augugcuggc aaucaaggga cccagaucac ggugaggac | 660 |
| cuuuuuuaca acauagccac gaggagaaaa gcuuuaaaaa auccaaguga agaauauggg | 720 |
| aaaauuuugg aaguuguugg cagguauuca guacacaaug caggcauuag uuucucaguu | 780 |
| aaaaaacaag gagagacagu agcugauguu aggacacuac ccaaugccuc aaccguggac | 840 |
| aauauucgcu ccaucuuugg aaaugcuguu agcgagaac ugauagaaau uggaugugag | 900 |
| gauaaaaccc uagccuucaa aaugaauggu acauauucca augcaaacua cucagugaag | 960 |
| aagugcaucu ucuuacucuu caucaaccau cgucugguag aaucaacuuc cuugagaaaa | 1020 |
| gccauagaaa cagugauge agccuauuug cccaaaaaca cacccauu ccuguaccuc | 1080 |
| aguuuagaaa ucaguccca gaauguggau guuaaugugc accccacaaa gcaugaaguu | 1140 |
| cacuuccugc acgaggagag cauccuggag cgggucagc agcacaucga gagcaagcuc | 1200 |
| cugggcucca auuccuccag gauguacuuc acccagacuu ugcuaccagg acuugcuggc | 1260 |
| cccucugggg agaugguuaa auccacaaca agcugaccu cgucuucuac uucuggaagu | 1320 |
| agugauaagg ucuaugccca ccagauggau cguacagauu cccgggaaca gaagcuugau | 1380 |

| | | |
|---|---|---|
| gcauuucugc agccucugag caaaccccug uccagucagc cccaggccau ugucacagag | 1440 |
| gauaagacag auauuucuag uggcagggcu aggcagcaag augaggagau gcuugaacuc | 1500 |
| ccagccccug cugaaguggc ugccaaaaau cagagcuugg aggggauac aacaaagggg | 1560 |
| acuucagaaa ugucagagaa gagaggaccu acuuccagca accccagaaa gagacaucgg | 1620 |
| gaagauucug auguggaaau gguggaagau gaucccgaa aggaaaugac ugcagcuugu | 1680 |
| accccccgga gaaggaucau uaaccucacu aguguuuuga gucuccagga agaaauuaau | 1740 |
| gagcagggac augagguucu ccgggagaug uugcauaacc acuccuucgu gggcugugug | 1800 |
| aauccucagu gggccuuggc acagcaucaa accaaguuau accuucucaa caccaccaag | 1860 |
| cuuagugaag aacuguucua ccagauacuc auuuaugauu ugccaauuu ggguguucuc | 1920 |
| agguuaucgg agccagcacc gcucuuugac cuugccaugc uugccuuaga uaguccagag | 1980 |
| aguggcugga cagaggaaga uggucccaaa gaaggacuug cugaauacau uguugaguuu | 2040 |
| cugaagaaga aggcugagau gcuugcagac uauuucucuu uggaaauuga ugaggaaggg | 2100 |
| aaccugauug gauuaccccu ucugauugac aacuaugugc ccccuuugga gggacugccu | 2160 |
| aucuucauuc uucgacuagc cacugaggug aauugggacg aagaaaagga auguuuugaa | 2220 |
| agccucagua agaaugcgc uauguucuau uccauccgga agcaguacau aucugaggag | 2280 |
| ucgacccucu caggccagca gagugaagug ccuggcucca uuccaaacuc cuggaagugg | 2340 |
| acugugaac acauugucua uaaagccuug cgcucacaca uucugccucc uaaacauuuc | 2400 |
| acagaagaug gaaauauccu gcagcuugcu aaccugccug aucuauacaa agucuuugag | 2460 |
| agguguuaaa uaugguuauu uaugcacugu gggaugguguu cuucuuucuc uguauuccga | 2520 |
| uacaaagugu uguaucaaag ugugauauac aaguguacc aacauaagug uugguagcac | 2580 |
| uuaagacuua uacuugccuu cugauaguau uccuuuauac acagugauu gauuauaaau | 2640 |
| aaauagaugu gucuuaacau aa | 2662 |

<210> SEQ ID NO 4
<211> LENGTH: 2271
<212> TYPE: DNA
<213> ORGANISM: Homo sapiens

<400> SEQUENCE: 4

| | | |
|---|---|---|
| atgtcgttcg tggcaggggt tattcggcgg ctggacgaga cagtggtgaa ccgcatcgcg | 60 |
| gcggggggaag ttatccagcg gccagctaat gctatcaaag agatgattga aactgtttta | 120 |
| gatgcaaaat ccacaagtat tcaagtgatt gttaaagagg gaggcctgaa gttgattcag | 180 |
| atccaagaca tggcaccgg atcaggaaa gaagatctgg atattgtatg tgaaaggttc | 240 |
| actactagta aactgcagtc ctttgaggat ttagccagta tttctaccta tggctttcga | 300 |
| ggtgaggctt tggccagcat aagccatgtg gctcatgtta ctattacaac gaaaacagct | 360 |
| gatgaaagt gtgcatacag agcaagttac tcagatggaa aactgaaagc ccctcctaaa | 420 |
| ccatgtgctg gcaatcaagg gacccagatc acggtggagg acctttttta caacatagcc | 480 |
| acgaggagaa aagctttaaa aaatccaagt gaagaatatg ggaaaatttt ggaagttgtt | 540 |
| ggcaggtatt cagtacacaa tgcaggcatt agtttctcag ttaaaaaaca aggagagaca | 600 |
| gtagctgatg ttaggacact acccaatgcc tcaaccgtgg acaatattcg ctccatcttt | 660 |
| ggaaatgctg ttagtcgaga actgataaa attggatgtg aggataaaac cctagccttc | 720 |
| aaaatgaatg gttacatatc caatgcaaac tactcagtga agaagtgcat cttcttactc | 780 |

```
ttcatcaacc atcgtctggt agaatcaact tccttgagaa aagccataga aacagtgtat    840
gcagcctatt tgcccaaaaa cacacaccca ttcctgtacc tcagtttaga aatcagtccc    900
cagaatgtgg atgttaatgt gcaccccaca aagcatgaag ttcacttcct gcacgaggag    960
agcatcctgg agcgggtgca gcagcacatc gagagcaagc tcctgggctc caattcctcc   1020
aggatgtact tcacccagac tttgctacca ggacttgctg gcccctctgg ggagatggtt   1080
aaatccacaa caagtctgac ctcgtcttct acttctggaa gtagtgataa ggtctatgcc   1140
caccagatgg atcgtacaga ttcccgggaa cagaagcttg atgcatttct gcagcctctg   1200
agcaaacccc tgtccagtca gccccaggcc attgtcacag aggataagac agatatttct   1260
agtggcaggg ctaggcagca agatgaggag atgcttgaac tcccagcccc tgctgaagtg   1320
gctgccaaaa atcagagctt ggaggggat  acaacaaagg ggacttcaga aatgtcagag   1380
aagagaggac ctacttccag caaccccaga aagagacatc gggaagattc tgatgtggaa   1440
atggtggaag atgattcccg aaaggaaatg actgcagctt gtaccccccg gagaaggatc   1500
attaacctca ctagtgtttt gagtctccag gaagaaatta atgagcaggg acatgaggtt   1560
ctccgggaga tgttgcataa ccactccttc gtgggctgtg tgaatcctca gtgggccttg   1620
gcacagcatc aaaccaagtt ataccttctc aacaccacca agcttagtga agaactgttc   1680
taccagatac tcatttatga ttttgccaat tttggtgttc tcaggttatc ggagccagca   1740
ccgctctttg accttgccat gcttgcctta gatagtccag agagtggctg gacagaggaa   1800
gatggtccca agaaggact  tgctgaatac attgttgagt ttctgaagaa gaaggctgag   1860
atgcttgcag actatttctc tttggaaatt gatgaggaag ggaacctgat tggattaccc   1920
cttctgattg acaactatgt gccccctttg gagggactgc ctatcttcat tcttcgacta   1980
gccactgagg tgaattggga cgaagaaaag gaatgttttg aaagcctcag taaagaatgc   2040
gctatgttct attccatccg gaagcagtac atatctgagg agtcgaccct ctcaggccag   2100
cagagtgaag tgcctggctc cattccaaac tcctggaagt ggactgtgga acacattgtc   2160
tataaagcct tgcgctcaca cattctgcct cctaaacatt tcacagaaga tggaaatatc   2220
ctgcagcttg ctaacctgcc tgatctatac aaagtctttg agaggtgtta a            2271
```

<210> SEQ ID NO 5
<211> LENGTH: 21
<212> TYPE: DNA
<213> ORGANISM: Artificial Sequence
<220> FEATURE:
<223> OTHER INFORMATION: primer
<400> SEQUENCE: 5
ggtctatgcc caccagattg t                                                21

<210> SEQ ID NO 6
<211> LENGTH: 21
<212> TYPE: DNA
<213> ORGANISM: Artificial Sequence
<220> FEATURE:
<223> OTHER INFORMATION: primer
<400> SEQUENCE: 6
ggtctatgcc caccagattg a                                                21

<210> SEQ ID NO 7
<211> LENGTH: 21
<212> TYPE: DNA
<213> ORGANISM: Artificial Sequence

```
<220> FEATURE:
<223> OTHER INFORMATION: primer

<400> SEQUENCE: 7
gttcaagcat ctcctcatct g                                              21

<210> SEQ ID NO 8
<211> LENGTH: 28
<212> TYPE: DNA
<213> ORGANISM: Artificial Sequence
<220> FEATURE:
<223> OTHER INFORMATION: PRIMER

<400> SEQUENCE: 8
ttctggaagt agtgataagg tctatgcc                                       28

<210> SEQ ID NO 9
<211> LENGTH: 19
<212> TYPE: DNA
<213> ORGANISM: Artificial Sequence
<220> FEATURE:
<223> OTHER INFORMATION: PRIMER

<400> SEQUENCE: 9
ggtttgctca gaggctgca                                                 19

<210> SEQ ID NO 10
<211> LENGTH: 10
<212> TYPE: DNA
<213> ORGANISM: Artificial Sequence
<220> FEATURE:
<223> OTHER INFORMATION: PRIMER

<400> SEQUENCE: 10
cagatggatc                                                           10

<210> SEQ ID NO 11
<211> LENGTH: 10
<212> TYPE: DNA
<213> ORGANISM: Artificial Sequence
<220> FEATURE:
<223> OTHER INFORMATION: PRIMER

<400> SEQUENCE: 11
cagatggttc                                                           10

<210> SEQ ID NO 12
<211> LENGTH: 20
<212> TYPE: DNA
<213> ORGANISM: Artificial Sequence
<220> FEATURE:
<223> OTHER INFORMATION: PRIMER

<400> SEQUENCE: 12
ggaagtagtg ataaggtcta                                                20

<210> SEQ ID NO 13
<211> LENGTH: 18
<212> TYPE: DNA
<213> ORGANISM: Artificial Sequence
<220> FEATURE:
<223> OTHER INFORMATION: PRIMER

<400> SEQUENCE: 13
ctgtcttatc ctctgtga                                                  18
```

```
<210> SEQ ID NO 14
<211> LENGTH: 18
<212> TYPE: DNA
<213> ORGANISM: Artificial Sequence
<220> FEATURE:
<223> OTHER INFORMATION: PRIMER

<400> SEQUENCE: 14
taaatccaca acaagtct                                                  18

<210> SEQ ID NO 15
<211> LENGTH: 21
<212> TYPE: DNA
<213> ORGANISM: Artificial Sequence
<220> FEATURE:
<223> OTHER INFORMATION: PRIMER

<400> SEQUENCE: 15
tagaaatatc tgtcttatcc t                                              21

<210> SEQ ID NO 16
<211> LENGTH: 23
<212> TYPE: DNA
<213> ORGANISM: Artificial Sequence
<220> FEATURE:
<223> OTHER INFORMATION: PROBE

<400> SEQUENCE: 16
ccaccagatg gttcgtacag att                                            23

<210> SEQ ID NO 17
<211> LENGTH: 23
<212> TYPE: DNA
<213> ORGANISM: Artificial Sequence
<220> FEATURE:
<223> OTHER INFORMATION: PROBE

<400> SEQUENCE: 17
ccaccagatg gatcgtacag att                                            23

<210> SEQ ID NO 18
<211> LENGTH: 18
<212> TYPE: DNA
<213> ORGANISM: Artificial Sequence
<220> FEATURE:
<223> OTHER INFORMATION: PROBE

<400> SEQUENCE: 18
caccagatgg ttcgtaca                                                  18

<210> SEQ ID NO 19
<211> LENGTH: 18
<212> TYPE: DNA
<213> ORGANISM: Artificial Sequence
<220> FEATURE:
<223> OTHER INFORMATION: PROBE

<400> SEQUENCE: 19
caccagatgg atcgtaca                                                  18

<210> SEQ ID NO 20
<211> LENGTH: 20
<212> TYPE: DNA
<213> ORGANISM: Artificial Sequence
<220> FEATURE:
<223> OTHER INFORMATION: PROBE
```

```
<400> SEQUENCE: 20
accagatggt tcgtacagat                                                    20

<210> SEQ ID NO 21
<211> LENGTH: 20
<212> TYPE: DNA
<213> ORGANISM: Artificial Sequence
<220> FEATURE:
<223> OTHER INFORMATION: PROBE

<400> SEQUENCE: 21
accagatgga tcgtacagat                                                    20

<210> SEQ ID NO 22
<211> LENGTH: 29
<212> TYPE: DNA
<213> ORGANISM: Artificial Sequence
<220> FEATURE:
<223> OTHER INFORMATION: PROBE

<400> SEQUENCE: 22
cttctggaag tagtgataag gtctatgcc                                          29
```